(12) United States Patent
Gleich et al.

(10) Patent No.: US 12,396,800 B2
(45) Date of Patent: Aug. 26, 2025

(54) SYSTEM FOR RECEIVING SIGNALS FROM A MAGNETO-MECHANICAL OSCILLATOR

(71) Applicant: KONINKLIJKE PHILIPS N.V., Eindhoven (NL)

(72) Inventors: Bernhard Gleich, Hamburg (DE); Jürgen Erwin Rahmer, Hamburg (DE); Ingo Schmale, Hamburg (DE); Tim Nielsen, Hamburg (DE); Richard Moessel, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 688 days.

(21) Appl. No.: 17/583,258

(22) Filed: Jan. 25, 2022

(65) Prior Publication Data
US 2022/0238011 A1  Jul. 28, 2022

(30) Foreign Application Priority Data
Jan. 25, 2021 (EP) .................................. 21153257

(51) Int. Cl.
*A61B 34/20* (2016.01)
*A61B 5/06* (2006.01)

(52) U.S. Cl.
CPC .............. *A61B 34/20* (2016.02); *A61B 5/062* (2013.01); *A61B 2034/2048* (2016.02); *A61B 2034/2051* (2016.02)

(58) Field of Classification Search
CPC .................. A61B 5/062; A61B 2034/2051
See application file for complete search history.

(56) References Cited

U.S. PATENT DOCUMENTS

| | | | |
|---|---|---|---|
| 2005/0216231 A1* | 9/2005 | Aoki ...................... | A61B 1/041 |
| | | | 702/183 |
| 2006/0084867 A1* | 4/2006 | Tremblay ............... | A61B 90/36 |
| | | | 600/434 |
| 2008/0132909 A1* | 6/2008 | Jascob ................... | A61B 34/20 |
| | | | 600/407 |
| 2020/0397320 A1* | 12/2020 | Gleich ............... | A61B 1/00158 |

* cited by examiner

*Primary Examiner* — Colin T. Sakamoto

(57) ABSTRACT

A system for receiving signals from a magneto-mechanical oscillator includes a main coil array adapted to receive a response signal of the magneto-mechanical oscillator and to transmit an excitation signal to the magneto-mechanical oscillator, and an additional coil for receiving a signal of the magneto-mechanical oscillator. A localizer is adapted to localize the additional coil and comprises a controller for controlling the main coil array and the additional coil such that a received localization signal is generated, a sensitivity provider for providing sensitivity information, and a processor for determining a position and/or orientation of the additional coil based on the provided sensitivity information and based on the received localization signal. A kit is provided for upgrading a system with a main coil array, by adding one or more additional coils and providing software for locating the one or more additional coils with the use of a pilot tone transmission.

18 Claims, 4 Drawing Sheets

SYSTEM FOR RECEIVING SIGNALS FROM A MAGNETO-MECHANICAL OSCILLATOR

CROSS-REFERENCES TO RELATED APPLICATIONS

This patent application claims priority to European Patent Application No. EP21153257, filed 25 Jan. 2021, the entirety of which is hereby incorporated by reference herein.

FIELD OF THE INVENTION

The invention relates to a system for receiving signals from a magneto-mechanical oscillator, wherein the system comprises a coil system and a localizer for localizing an additional coil of the system, the coil system, and the localizer. Further, the invention refers to a method and a computer program for localizing the additional coil of the system.

BACKGROUND OF THE INVENTION

Recently, very small mechanical devices have been developed, for instance, in the form of microrobots or microdevices, that can be advantageously utilized in applications that introduce a strict size constraint, for instance, medical applications within the human body. Such microdevices are in particular useful in the form of localization or sensor devices. A very advantageous kind of such microdevices refers to magneto-mechanical oscillators that have recently been introduced. A localization or sensing of such magneto-mechanical oscillators relies on a spatially resolved detection of response signals of the magneto-mechanical oscillator sent in response to an excitation signal. Information on a location of the magneto-mechanical oscillator is typically obtained by using an array of receiving coils with a known spatial sensitivity profile. In this context, in most applications, a compromise has to be found between the spatial resolution provided by the coil array and the technical effort that has to be invested into the coil array and the detection system, wherein this compromise often leads to a limited number of rather large detection coils which are good enough for most applications. However, for some applications, a higher resolution may be needed for a short time period, for instance, during a time period in which a fine needle has to be inserted into a patient. Finer coil arrays would provide a higher resolution and sensitivity especially if they were provided close to the workspace and might be suitable for such applications. However, due to the technical effort that has to be invested into these finer coil arrays and since they may interfere with the workflow of an interventional procedure, it is inconvenient to use finer coil arrays all the time. It would thus be desired to provide a detection system for magneto-mechanical oscillators that can be applied more flexibly in medical applications and is easily adapted to different medical situations.

SUMMARY OF THE INVENTION

It is therefore an object of some embodiments of the present invention to provide a system for receiving signals from a magneto-mechanical oscillator that can be applied more flexibly in medical applications and can be adapted to different medical situations. Moreover, it is an object of some embodiments of the application to provide a coil system, a localizer, a method and a computer program that can be utilized in such a system.

According to a first aspect of the invention, a system for receiving signals from a magneto-mechanical oscillator is presented, wherein the system is adapted to be used in a medical application and comprises a) a main coil array comprising a main receiving coil adapted to receive an electromagnetic response signal of the magneto-mechanical oscillator and a main sending coil adapted to send an electromagnetic excitation signal for exciting the magneto-mechanical oscillator, b) an additional coil adapted to receive an electromagnetic response signal of the magneto-mechanical oscillator and/or to send an electromagnetic excitation signal for exciting the magneto-mechanical oscillator, and c) a localizer adapted to localize the additional coil, wherein the localizer comprises i) a controller adapted a) to control the main sending coil to send an electromagnetic localization signal that is receivable by the additional coil and to control the additional coil to generate a received localization signal indicative of the electromagnetic localization signal received by the additional coil, and/or b) to control the additional coil to send an electromagnetic localization signal that is receivable by the main receiving coil and to control the main receiving coil to generate a received localization signal indicative of the electromagnetic localization signal received by the main receiving coil, ii) a sensitivity provider adapted to provide a sensitivity information that is indicative of a sensitivity profile of a) the additional coil and the main sending coil, respectively, if the main sending coil is controlled to send the electromagnetic localization signal, and/or b) the additional coil and the main receiving coil, respectively, if the additional coil is controlled to send the electromagnetic localization signal, and iii) a processor adapted to determine a position and/or orientation of the additional coil based on the provided sensitivity information and based on the received localization signal.

Since the system provides an additional coil for receiving an electromagnetic response signal of the magneto-mechanical oscillator and/or for sending an electromagnetic excitation signal, the receiving characteristics and setup of the coil array can be adapted to different situations. Moreover, since the system further comprises a localizer that is adapted to localize the additional coil based on the provided sensitivity information and based on the received localization signal, the integration of the additional coil in an already existing main coil array for localizing the magneto-mechanical oscillator becomes easy and can be performed in a short time period such that the application of the system in a medical environment becomes even more flexible. Thus, the system can be applied flexibly and can be adapted to different medical situations.

Generally, magneto-mechanical oscillators are provided in the form or as part of milli- or even microdevices that can be utilized in applications with spatial restrictions, in particular, in interventional applications within the human being. For example, such magneto-mechanical oscillators can be used as part of catheters or needles that are introduced into a human body, wherein the magneto-mechanical oscillators allow for an accurate localization of the catheters or needles. Moreover, the magneto-mechanical oscillators can also be applied together with or as part of other interventional devices like implants or other medical interventional instruments. Further, magneto-mechanical oscillators are not only provided for localization purposes but can also be applied as sensor devices for sensing physical parameters in an environment of the magneto-mechanical oscillator.

Generally, a magneto-mechanical oscillator comprises a magnetic object that can rotate or oscillate when subjected to an excitation electromagnetic field. The rotating or oscillating magnetic object then generates itself a signal in form of a periodically changing electromagnetic response field that can be measured, for instance, outside of a patient in which the magneto-mechanical oscillator is implanted. In some applications, additional information like measurements of physical parameters in the environment of the magneto-mechanical oscillator or an identification of the magneto-mechanical oscillator can be encoded in the response signal. An example of a pressure sensor comprising a magneto-mechanical oscillator can be found, for instance, in WO 2019243098 A1.

The main coil array refers to a coil array that is utilized in medical applications of the system for receiving the signals of the magneto-mechanical oscillator. It comprises a main receiving coil that is adapted to receive an electromagnetic response signal of the magneto-mechanical oscillator and a sending coil adapted to send an electromagnetic excitation signal for exciting the magneto-mechanical oscillator. Beneficially, the main coil array comprises more than one main receiving coil; beneficially a main receiving coil array with at least three main receiving coils for receiving the electromagnetic response signal of the magneto-mechanical oscillator in order to allow for an accurate localization of the magneto-mechanical oscillator. Moreover, the main coil array can also comprise more than one main sending coil, for instance, a main sending coil array, for sending electromagnetic excitation signals from different directions to the magneto-mechanical oscillator. Beneficially, a main receiving coil is adapted such that it can also be utilized as a main sending coil for sending the electromagnetic excitation signal and a main sending coil is adapted such that it can also be utilized as a main receiving coil for receiving the electromagnetic response signal from the magneto-mechanical oscillator. In the following embodiment, all coils that belong to the main coil array, i.e. all main receiving coils and all main sending coils, will be referred to as main coils, if an embodiment can be applied to both the main receiving coil and the main sending coil. In this case, the respective embodiment or characteristic described with respect to a "main coil" can be applied to at least one of the main coils or, beneficially, to all of the main coils. All embodiments referring to a main coil can be applied to the main receiving coil and/or the main sending coil.

In an embodiment, the main coil array comprises main coils that can be used both as main receiving coils and as main sending coils and that are arranged in form of a 3 times 3, or more beneficially, a 4 times 4, array arrangement. A 3 times 3 array arrangement refers to a rectangular grid with 3 times 3 grid areas, wherein in each grid area a main coil is arranged such that all in all nine main coils are arranged in the main coil array in a regular grid pattern. A 4 times 4 array arrangement is similar to the 3 times 3 arrangement, but instead of nine, sixteen coils are arranged in the main coil array in a regular grid pattern. However, the main coils of the main coil array can also be arranged in other patterns, for instance, can be arranged in a hexagonal pattern. Moreover, the main receiving coils and the main sending coils can also be arranged in independent patterns. For example, the main sending coils can be arranged in a hexagonal pattern, whereas the main receiving coils are arranged in a rectangular pattern. In such a case, the two arrangement patterns can overlap in the same plane, can be arranged side by side, or can be arranged in different planes of an area of interest. For example, a main sending coil or main sending coil array can be arranged above the patient and a main receiving coil or a main receiving coil array can be arranged below the patient. Generally, the main coil array can comprise a supporting structure on which the main coils or at least a part of the main coils, for example, the main receiving coils, are arranged in order to support one or more predetermined arrangements of the main coil array. Beneficially, such a supporting structure can be adapted to the outline of a patient or a patient support. For example, the supporting structure can be flexible or can be bent or can be generally deformable. This allows to also apply a main coil array in a flexible manner. Moreover, in a beneficial embodiment the main coil array is integrated into a patient support on which a patient is supported during a medical procedure.

Generally, the main coil array is adapted to be used in a medical application. For example, the main receiving coil and the main sending coil can be provided with a biocompatible housing that allows to position the main receiving coil and the main sending coil in direct contact with tissue of a patient. Moreover, the main coil array can be adapted to fulfill the hygiene requirements in an interventional area or in a general care environment. Beneficially, the main coils of the main coil array, for example, the main receiving coil and the main sending coil, comprise a diameter between 10 cm to 20 cm. In some embodiments, the main coils can comprise different diameters. For example, the main sending coil can have a different diameter than the main receiving coil. Beneficially, the main coils of the main coil array have an extent in the magnetic axis direction below 5 mm, more beneficially below 2 mm, and even more beneficially below 1 mm. In an embodiment, the main coils of the main coil array refer to flat coils, i.e. planar coils in which all windings are provided in the same plane. However, beneficially, the main coils comprise at least two winding layers. This allows to avoid the problem of planar coils with only one winding layer to contact the innermost layer. Further, it is beneficial that the main coils of the main coil array are adapted to be applicable also in medical environments and situations with strict weight constrains and/or that the main coils of the main coil array are invisible for X-rays. Beneficially the main coils of the main coil array are made at least partly of aluminum. Beneficially, the inductance of the main coils of the main coil array is smaller than 200 µH, and more beneficially smaller than 50 µH. Such small inductances allow to keep an operating voltage small, which allows to also keep the isolation requirements for the coils small.

Further, the system comprises an additional coil that is adapted to receive an electromagnetic response signal of the magneto-mechanical oscillator and/or to send an electromagnetic excitation signal for exciting the magneto-mechanical oscillator. The additional coil could be a separate coil, i.e. generally not part of the main coil array and not used in all medical applications of the system. This coil can be added if necessary, for instance, if a higher spatial resolution for the localization of the magneto-mechanical oscillator is desired. Generally, the additional coil may be adapted to be used in a medical application. For example, the additional coil can be provided with a biocompatible housing that allows to position the additional coil in direct contact with tissue of a patient. Moreover, the additional coil can be adapted to fulfill the hygiene requirements in an interventional area or in a general care environment. The additional coil can comprise the same characteristics of a main coil used in the main coil array as described above. Alternatively, the additional coil can comprise different characteristics in comparison to the main coil. Moreover, different additional coils may be provided by the system for different medical applications of the system.

In accordance with some embodiments of the main coil array, it is beneficial that also the additional coil is adapted to be applicable in medical environments and situations with strict weight constrains and/or that the additional coil is invisible for X-rays. It is also beneficial that the additional coil is made at least partly of aluminum. Beneficially, the additional coil has a diameter that is smaller than the diameter of the main coils of the main coil array. Beneficially, the diameter of the additional coil is adapted to its intended application. In particular, if only one additional coil is provided, the diameter of the additional coil refers substantially to the expected maximal distance between the magneto-mechanical oscillator and the additional coil during the application of the additional coil. For example, if it is expected that in an interventional procedure a needle is provided maximally 3 cm below the skin of a patient, wherein the additional coil is arranged directly on the skin of the patient, the additional coil may have, beneficially, a diameter of 3 cm. In case more than one additional coil is provided, for instance, an additional coil array, the diameter of the additional coils of the additional coil array can generally be smaller than the diameter of only one additional coil. In particular, the diameter of the additional coils of an additional coil array can refer substantially to between 0.1 and 0.5 times the expected maximal distance between the magneto-mechanical oscillator and the additional coil array during the application of the additional coil array. In both above-described embodiments, the diameter of the additional coils can be provided with a deviation from the preferred diameter of up to a factor of two of the preferred diameter. The inventors have found that also for such deviations the electromagnetic response signal of the magneto-mechanical oscillator can be detected by the additional coil with a suitable accuracy.

If the additional coil is only adapted for receiving the electromagnetic response signal of the magneto-mechanical oscillator, it is beneficial that the additional coil comprises an inductance that is higher than the inductance of the main receiving coil, and beneficially an inductance that is higher than 1 mH. This allows for an easy amplification of the received electromagnetic response signal and/or for utilizing, if necessary, a less complex connecting cable to a receiving unit for further processing of the signals. In an embodiment, in which the additional coil is also adapted for sending an electromagnetic excitation signal, it is beneficial that the additional coil comprises the same inductance as the main sending coil, beneficially an inductance smaller than 200 μH, and more beneficially smaller than 50 μH. The additional coil can refer to a flat, even planar coil, as also beneficial for the main coils of the main coil array, but can also refer to a cylindrical coil.

The additional coil is generally adapted to be placed in a region of interest, i.e. in a region near the magneto-mechanical oscillator. Beneficially, the additional coil is adapted to be attached to a region of interest of a living being. For example, the additional coil can be adapted to provide attachment means that allow such an attachment to a region of interest of a living being. Such attachment means can refer, for instance, to skin adhesives, straps, tapes, etc. that can be utilized for attaching an object to the skin of a living being.

In a beneficial embodiment, the system comprises more than one additional coil, and beneficially an additional coil array comprising at least two additional coils. In an embodiment, the additional coils are adapted to be provided freely in a spatial region, i.e. the additional coils comprise no fixed spatial relation to each other and can be set, for instance, per hand by a user into a spatial arrangement that is suitable for the respective application. However, in another beneficial embodiment, the additional coils can be adapted such that they provide a predetermined spatial relation to each other. For example, the additional coils can be arranged on a mounting support that supports the positioning of the additional coils at predetermined positions. For example, the mounting support can be adapted such that the distances and positions of the additional coils with respect to each other are fixed. However, the mounting support can also allow for a certain flexibility, for instance, for arranging the additional coils in a plurality of different spatial arrangements that are predetermined by the structure of the mounting support. The mounting support can also provide measurement means that allow to measure a spatial relation between the additional coils of the additional coil array. For example, the mounting support can refer to a folding mounting support that comprises sensors for determining an angle between different structures of the folding mounting support, wherein the mounting support is enfolded for being arranged in a region of interest.

Providing the additional coils with generally known spatial relations to each other has the advantage that in the application of the system only the location of one of the additional coils has to be determined, wherein then, due to the known spatial relation between all of the additional coils, directly also the locations of the other additional coils are known. This allows for a fast integration of the additional coils into the main coil array, in applications in which timing might be important. Additionally or alternatively, the processor can be adapted to determine a position and/or orientation of all additional coils based on the sensitivity information and the received localization signals by directly taking the spatial relation into account. For example, the spatial relation can be used to determine starting positions and/or orientations for all the additional coils and the processor can then be adapted to solve the equations for determining the positions and/or orientations of the additional coils in dependency of each other based on these starting points. This allows to determine the positions and/or orientations of all the additional coils more accurately.

Moreover, the processor can also be adapted to determine based on all received localization signals of the additional coils, the sensitivity information and the spatial relation between the additional coils whether an object might be present in the vicinity of the additional coil array that leads to a distortion of the electromagnetic field in the vicinity of the additional coil array. Such an object, for instance, a magnetic or magnetizable object, may decrease the accuracy of determining not only the position and/or orientation of the additional coils but also of the magneto-mechanical oscillator. In particular, the processor can be adapted to compare a determined relative position and/or orientation of the additional coils with respect to each other with the known spatial relation of the additional coils, i.e. the known relative position and/or orientation with respect to each other. If the comparison results in a deviation of a position and/or orientation of one or more of the additional coils from the known spatial relation that is greater than expected, due to the always present noise, for instance, greater than a predetermined acceptable deviation range, then the processor can be adapted to determine that an object is present that leads to a distortion in an electromagnetic field in the area of interest. In this case, the processor can be adapted to assume that the position of the object is static, i.e. not moving, and comprises a linear magnetization. Based on these assumptions, the processor can be adapted to determine a compensation for the presence of the object such that, when applying the compensation, the determined relative positions and/or orientations of the additional coils correspond to the known spatial relation of the additional coils. For example, the processor can utilize a dipole model for modelling the influence of a magnetic or magnetizable object in the area of interest. In this example, a dipole is added as representation for the magnetic object to a model describing the electromagnetic fields of the main coils and the additional coils, and the added dipole is provided with a magnetic time delay expected for eddy currents in a magnetic or magnetizable object, wherein then the position, strength and phase of the added dipole in the model can be adjusted until determination of the positions and/or orientations of the additional coils taking the dipole model into account leads to an acceptable accuracy, i.e. a deviation from the known spatial relation below a predetermined threshold. However, the processor can also apply any other method for providing a correction of the distortion caused by the presence of the magnetic or magnetizable object. Moreover, although the above assumptions lead to accurate results in the context of medical applications, while allowing for an easy and computationally less expensive determination of the correction of the distortion, also other assumptions, in particular, more complex assumptions can be used to model the presence of the magnetic or magnetizable object. Furthermore, although described with respect to the above-described additional coil array, distortions in the magnetic field can also be determined and corrected based on only one additional coil. For example, in this case the additional coil can be placed successively at different positions and/or orientations in the area of interest that have a known spatial relation to each other. The above principles can then be applied to the determination of the successive positions and/or orientations of the additional coil compared with the known spatial relation of these successive positions and/or orientations. Generally, the processor can also be adapted to indicate the presence of such a magnetic or magnetizable object to a user of the system and prompt the user to remove the object, if possible. However, the processor can also be adapted, based on the determined distortion of the magnetic field, to correct for the distortion of the magnetic field during the localizing of the magneto-mechanical oscillator, for instance, if a removal of the object is not possible. In particular, such distortions and the corresponding corrections can be determined accurately if the additional coil or the additional coil array is placed at different positions in the area of interest and the determination of the distortion is repeated for each position of the additional coil or the additional coil array. Due to the easy and flexible system that allows to utilize the additional coil in this way, distortions in the electromagnetic field that can be relevant for the receiving of the electromagnetic response signal of the magneto-mechanical oscillator can be accurately and easily detected, which allows for a correction of the distortions and for a more accurate determination of, for instance, the location of the magneto-mechanical oscillator.

Further, the system comprises a localizer adapted to localize the additional coil. The localizer beneficially may be formed as part of hardware and/or software of a computing device. The computing device can refer to any known general or dedicated computing device, for instance, to a personal computer, a handheld computer like a smartphone, a tablet, a laptop, etc., a cloud computing device, etc. Beneficially, the localizer is part of a hardware and/or software of a computing device that is already utilized for determining a localization of the magneto-mechanical oscillator. However, the localizer can also be part of a dedicated computing device not performing any other task.

The localizer comprises a controller that is adapted to control the main sending coil to send an electromagnetic localization signal that can be received by the additional coil and to control the additional coil to generate a received localization signal indicative of the electromagnetic localization signal received by the additional coil. Additionally or alternatively, the controller is adapted to control the additional coil to send an electromagnetic localization signal that can be received by the main receiving coil and to control the main receiving coil to generate a received localization signal indicative of the electromagnetic localization signal received by the main receiving coil. The additional coil can be localized by receiving a signal sent by the main sending coil or by itself sending a signal that can then be received by the main receiving coil. In both cases, the received localization signal is indicative of the electromagnetic localization signal received by the main receiving coil and/or the additional coil, respectively, and is hence also indicative of the location and/or orientation at which the additional coil is arranged in relation to the main coil array. The electromagnetic localization signal can be any signal that is suitable for localizing the additional coil, i.e. any signal that can be received by the additional coil and/or the main receiving coil. For example, the electromagnetic localization signal can refer to the electromagnetic excitation signal used for exciting the magneto-mechanical oscillator. However, the electromagnetic localization signal can also refer to a signal only used for localizing the additional coil, wherein the electromagnetic localization signal can the comprise signal characteristics that are in particularly suitable for the localization of the additional coil. Beneficially, the electromagnetic localization signal refers to a sequence of electromagnetic pulses, wherein the sequence of pulses can comprise different pulse patterns, for instance, by varying the time between two subsequent pulses.

The localizer further comprises a sensitivity provider that is adapted to provide sensitivity information that is indicative of a sensitivity profile of a) the additional coil and the main sending coil, respectively, if the main sending coil is controlled to send the electromagnetic localization signal, and/or b) the additional coil and the main receiving coil, respectively, if the additional coil is controlled to send the electromagnetic localization signal. Generally, if more than one additional coil is provided, the sensitivity provider can be adapted to provide a sensitivity information that is indicative of the sensitivity profiles of all the additional coils. Moreover, if more than one main receiving coil and/or more than one main sending coil is provided, the sensitivity provider can be adapted to provide sensitivity information that is indicative of the sensitivity profiles of all main receiving coils and/or all main sending coils, respectively. In particular, the sensitivity provider is adapted to provide the sensitivity information that is necessary for determining the position and/or orientation of the additional coil. For example, if the controller is adapted to control the main sending coil for providing the electromagnetic localization signal, then the sensitivity provider is adapted to provide sensitivity information that is indicative of sensitivity profiles of the additional coil and the main sending coil. In another example, if the controller is adapted to control the additional coil to send the electromagnetic localization signal, the sensitivity provider is adapted to provide sensitivity information indicative of the sensitivity profiles of the main receiving coil and the additional coil. Accordingly the sensitivity provider is adapted to provide sensitivity information that is indicative of the sensitivity profile of the coil or coils sending the electromagnetic localization signal and the sensitivity profile of the coil or coils receiving the electromagnetic localization signal.

A sensitivity profile generally refers to a flux density of a magnetic field generated by a coil supplied with a predetermined current in an area of interest, for instance, in a 3D area with a predetermined distance around the respective coil. The sensitivity profile of a coil can generally be frequency dependent, i.e. can depend on the frequency of a current supplied to the coil. In this case, it is beneficial that the sensitivity provider provides the sensitivity information such that it is indicative of the sensitivity profile at frequencies that are expected to be used for the electromagnetic localization signal. Generally, the sensitivity profile is the same, independent on whether the coil is used as a sending coil or as a receiving coil. Providing the sensitivity information such that it is indicative of the sensitivity profiles of the respective coils in an area of interest allows to determine the position of the additional coil with an accuracy that is higher than the size, for instance, diameter, of the additional coil itself. In an embodiment, the sensitivity information can directly be the respective sensitivity profile. However, in a beneficial embodiment the sensitivity information is provided in form of positions of electric conductors in an area of interest that provide a magnetic field, i.e. a flux density, with a sensitivity profile of the respective coil when provided with a predetermined current. In this case the sensitivity profile is represented by the positions of the respective electric conductors and the positions are thus indicative of the sensitivity profile. Alternatively, the sensitivity information can refer to information on the positions of dipoles in the area of interest that provide a magnetic field that can represent the sensitivity profile of a respective coil.

The localizer further comprises a processor that is adapted to determine a position and/or orientation of the additional coil based on the sensitivity information and based on the received localization signal. In particular, the processor is adapted to determine the position and/or orientation of the additional coil in relation to the position and/or orientation of the coils of the main coil array. If the positions and/or orientations of the coils of the main coil array are known in a global coordinate system, it is beneficial that also the position and/or orientation of the additional coil is determined in the global coordinate system based on the determined spatial relation between the additional coil and the coils of the main coil array. Generally, methods for localizing, for instance, a sensor providing an electromagnetic signal, using a coil array are known. In particular, the processor can be adapted to utilize an algorithm that is similar to the algorithm used for localizing the magneto-mechanical oscillator. For instance, the processor can be adapted to determine the position and/or orientation of the additional coil based on the sensitivity information that is indicative of the respective sensitivity profiles and the received localization signal by utilizing the Biot-Savart law, for example, in accordance with the methods described in the article "Electromagnetic navigation in medicine—basic issues, advantages and shortcomings, prospects of improvement" by M. Baszyński et al., Journal of Physics: Conference Series, volume 238, pages 1 to 11 (2010). However, also other algorithms can be utilized for determining the position and/or orientation of the additional coil.

In an embodiment, the additional coil comprises a receiving circuitry for receiving an electromagnetic excitation signal sent by the main sending coil and generating an electrical signal indicative of the received electromagnetic signal, wherein the receiving circuitry is adapted for operating within a certain range and not reaching a saturation threshold for the receiving circuitry when receiving the electromagnetic excitation signal sent by the main sending coil, and generating an electrical signal indicative of the received electromagnetic excitation signal. The receiving circuitry can comprise software and/or hardware that is adapted to transduce an electromagnetic signal received by the additional coil into an electrical signal that is indicative of the received electromagnetic signal. For instance, an electrical signal that comprises a functional relationship to the received electromagnetic signal, like a proportional relationship, a quadratic relationship, etc. Generally, it is known that software and/or hardware-based circuitry used for transducing an electromagnetic signal received, by a coil to an electrical signal, has a threshold for the received electromagnetic signal amplitudes and that received electromagnetic signal amplitudes which are at and above this threshold cannot be distinguished from each other. In other words, the generated electrical signal for received electromagnetic signal amplitudes which are at and above the threshold is not indicative of different amplitudes of the received electromagnetic signal. In the context of receiving the electromagnetic response signals of magneto-mechanical oscillators, it would need to be taken into account that the electromagnetic excitation signal for exciting magneto-mechanical oscillators needs to provide a relatively high amplitude to get an electromagnetic response signal from the magneto-mechanical oscillator. However, at the same time, the electromagnetic response signal sent by the magneto-mechanical oscillator is generally some magnitudes lower in amplitude than the electromagnetic excitation signal. For example, the electromagnetic excitation signal can have a flux density of approximately 1 µT to 1 mT, whereas the electromagnetic response signal approximately has a flux density of 1 pT to 100 nT. It is beneficial that coils, like the additional coil, used for receiving an electromagnetic response signal from the magneto-mechanical oscillator, are adapted to receive the relatively low amplitudes of the signal sent by the magneto-mechanical oscillator. Accordingly, the receiving circuitry can be adapted to receive the electromagnetic response signals with relatively low amplitude of the magneto-mechanical oscillator. In this case, the magneto-mechanical oscillator would be saturated when subjected to an electromagnetic excitation signal a with higher amplitude, that is used, for instance, for locating the additional coils. However, the receiving circuitry can be adapted such that it is not saturated when subjected to the electromagnetic excitation signal sent by the sending coil. For example, the receiving circuitry of the additional coil may comprise a damping element that is adapted for damping a received signal, beneficially only damping received signals exceeding a predetermined signal amplitude, such that the saturation threshold for the receiving circuitry is reduced and not reached by the electromagnetic excitation signal which is sent by the sending coil. As a non-limiting example, the damping element can be a voltage divider or an adjustable voltage divider comprising two resistors in series and a contact in-between. In another example, instead of a resistor-based voltage divider, an inductive or capacitive voltage divider can be utilized for damping the received signal.

Beneficially, the damping element allows for a damping of the received signal with a damping factor of 100, more beneficially 1,000, and even more beneficially 1,000,000. Beneficially, the damping element can be a variable damping element type, which means that damping factor can be adjustable between different damping factor values, for instance, adjustable to be within a range of between 1,000 and 100,000. Since without damping, elements commonly employed in a receiving circuitry are adapted to generate an electrical signal indicative of a received electromagnetic signal over a received amplitude range of approximately 4 to 5 orders of magnitude, providing the damping element allows to increase the possible range such that the electromagnetic excitation signal and the response signal can be processed by the receiving circuitry. Moreover, also different receiving paths can be provided by the receiving circuitry that can be automatically selected based on the amplitude of the received electromagnetic signal, wherein each of the receiving paths are particularly adapted for a specific amplitude range of the received electromagnetic signal. Because of this, the frequency with which localization measurement can be performed could be maximized. This is due to the fact that the measurements for relative localizations can be performed in any point in time. This could mean that no additional time would be required for separate localization measurements as the procedure does not need to be supplemented by additional point-in-time measurements. For instance, the additional coil localization could be performed simultaneously with sending the excitation pulse for localizing the position of the coil or the apparatus. The relative localization can be done during any of the time intervals.

In an embodiment, the receiving circuitry comprises an adjustable damping element that is adapted for adjusting a damping factor for damping the received signal. In this case, it is beneficial that the receiving circuitry is adapted such that an adjustment of the damping factor leads to an impedance change in the receiving circuitry that lies below a predetermined threshold. In particular, the predetermined threshold is determined such that an impedance change of the receiving circuitry below the threshold leads to a still acceptable accuracy when determining the position and/or orientation of the additional coil. Such impedance changes in the receiving circuitry can lead to changes in the reception currents caused by the electromagnetic localization signal in the additional coil connected to the receiving circuitry and lead to an inaccurate reception of the electromagnetic localization signal that can lead to an inaccurate localization of the additional coil. Additionally and alternatively for this case, the processor can be adapted to correct for impedance changes caused by the adjustable damping element in the receiving circuitry. For example, the sensitivity information can be determined and provided for the additional coil for each damping factor provided by the adjustable damping element, respectively, and the processor can then be adapted to take the sensitivity information with respect to a current damping factor into account when determining the position and/or orientation of the additional coil. Moreover, the damping element can also be realized as an inductance coupling that leads to a damping of a received signal by the characteristics of the involved inductances.

In an embodiment, the additional coil comprises a sending circuitry adapted to generate from a provided electrical signal a current in the coil that allows for the sending of an electromagnetic signal, wherein the sending circuitry is adapted such that two sending paths are provided, wherein the first sending path is adapted to generate from the provided electric signal a current in the coil that allows for the sending of the electromagnetic localization signal and wherein the second sending path is adapted to generate from the provided electric signal a current in the coil that allows for the sending of the electromagnetic excitation signal. The sending circuitry can comprise software and/or hardware that is adapted to transduce the electric signal received, for instance, from a computer interface, into a current that is applied to the additional coil for generating a sending signal. Beneficially, the sending circuitry and the receptor circuitry are combined to a sending/receiving circuitry of the additional coil. Moreover, the above described receiving circuitry and/or sending circuitry can also be provided in the coils of the main coil array, i.e. in the main receiving coil and the main sending coil.

In an embodiment, the controller is adapted to control the main sending coil and/or the additional coil such that the electromagnetic localization signal is sent repeatedly with a predetermined time period between each electromagnetic localization signal and to control the additional coil and/or the main receiving coil, respectively, to generate a received localization signal based on each received electromagnetic localization signal. Accordingly, the controller is adapted a) to control the sending coil such that the electromagnetic localization signal is sent repeatedly with a predetermined time period between each electromagnetic localization signal and the additional coil to generate a received localization signal based on each received electromagnetic localization signal and/or b) to control the additional coil such that the electromagnetic localization signal is sent repeatedly with a predetermined time period between each electromagnetic localization signal and the main receiving coil to generate a received localization signal based on each received electromagnetic localization signal, and the processor is adapted to determine a position and/or orientation of the additional coil based on the generated received localization signals. Sending the electromagnetic localization signal repeatedly with a predetermined repetition frequency, i.e. a predetermined time period between each electromagnetic localization signal, has the advantage that a position and/or orientation of the additional coil can be determined not only once, for instance, at the beginning of an interventional procedure, but repeatedly over the time period the additional coil is applied. In particular, in applications, in which at least some movement of the additional coil is to be expected, determining the position and/or orientation of the additional coil repeatedly after predetermined time periods allows to determine the position and/or orientation of the additional coil more accurately and accordingly also to determine a location of the magneto-mechanical oscillator more accurately. In particular, the predetermined time period between the repeatedly sent electromagnetic localization signals, i.e. the frequency with which a localization signal is repeated, beneficially can be adapted by the controller to the respective application of the additional coil. For example, the controller can be adapted to select from a plurality of predetermined time periods the time period that lies within the time scales expected for a respective application. In particular, a user can indicate for which application the additional coil shall be utilized and the controller can then be adapted to select the predetermined time period based on the input of the user. For instance, if only slow movements on the time scales of at least some minutes are expected in a region in which the additional coil is placed, the controller can be adapted to select a predetermined time period that refers approximately to one minute to ensure that a current position and/or orientation of the additional coil is accurately determined. However, for applications in which smaller time scales are expected, for instance, if an additional coil is placed at a chest region of a patient such that breathing motion is expected, the controller can be adapted to select a predetermined time period that lies within a few second for accurately tracking the position and/or orientation of the additional coil.

In an embodiment, the controller is adapted to control the sending coil and/or the additional coil to send the electromagnetic localization signal continuously and to generate a received localization signal continuously based on the received electromagnetic localization signal. Advantageously, in this embodiment, the processor also can be adapted to determine a position and/or orientation of the additional coil substantially continuously based on the continuous received localization signal. This allows for an accurate tracking of the position and/or orientation of the additional coil. This is particularly desirable in applications in which an accurate localization is needed in strongly changing or fluctuating environments, for instance, in a circulatory blood system of a patient in an, e.g., interventional procedure near a heart of a patient.

In an embodiment, the main sending coil refers to a main sending coil array comprising a plurality of main sending coils, and the controller is adapted to control the main sending coil array. This may done in a way such that each of the coils of the main sending coil array subsequently sends an electromagnetic localization signal, and the additional coil is used to generate a received localization signal for each of the sequentially received electromagnetic localization signals. Additionally, or alternatively, the additional coil refers to an additional coil array comprising a plurality of additional coils, and the controller is adapted to control the additional coil array such that each of the additional coils of the additional coil array subsequently sends an electromagnetic localization signal, and the main receiving coil generates received localization signal for each of the sequentially received electromagnetic localization signals. The processor is then adapted to further determine a position and/or orientation of the additional coil based on each of the generated received localization signals. Accordingly, if more than one coil, either more than one sending coil or more than one additional coil is provided in the system (where there is at least one sending coil and at least one additional coil), the controller is adapted to control the respective coils to subsequently send electromagnetic localization signals. In other words, the controller is adapted to control a first coil to send a first electromagnetic localization signal, then a second coil to send a second electromagnetic localization signal, then a third coil sending a third electromagnetic localization signal, etc. Determining the position based on each of the generated received localization signals allows for a much more accurate localization of the position and/or orientation of the additional coil. Beneficially, in this embodiment the sent electromagnetic localization signals are similar to each other, for instance, comprising the same signal characteristics, like signal frequency, amplitude, length, etc. However, in other embodiments, the electromagnetic localization signals can also be different for each coil, for instance, each coil can be controlled to send an electromagnetic localization signal that differs from the electromagnetic localization signal sent from another coil. It is further noted that in both embodiments described above also the coils receiving the localization signal can refer to a coil array. For example, if the main sending coil refers to a main sending coil array, also the additional coil can refer to an additional coil array such that each of the additional coils of the additional coil arrays receives the sequentially sent electromagnetic localization signals, wherein the position determination unit is then adapted to determine a position and/or orientation of the additional coil array, i.e. of all additional coils, based on each of the generated received localization signals. Alternatively to sending the electromagnetic localization signals sequentially, the controller can also be adapted to control either the main sending coil array or the additional coil array, respectively, to send the electromagnetic localization signals at the same time. In order to avoid a saturation of a receiving circuitry of the respective receiving coil, i.e. the main receiving coil or the additional coil, it is beneficial in this embodiment that the electromagnetic localization signals sent by different coils have different frequencies. In another beneficial embodiment, the electromagnetic localization signal comprises to a sequence of electromagnetic pulses, wherein the sequence of pulses can comprise different pulse patterns, for instance, by varying the time between two subsequent pulses. It is then beneficial that the controller is adapted to control each coil, i.e. the main sending coils or the additional coils, respectively, to send an electromagnetic localization signal comprising for different coils different pulse patterns. Accordingly, while sending the electromagnetic localization signals at the same time, not all pulses belonging to the electromagnetic localization signals are sent at the same time and, hence, are received by the respective coils at the same time such that a saturation can be avoided. Moreover, utilizing different frequencies or different pulse patterns also allows to encode an identity of the coil that has sent the respective electromagnetic localization signal and accordingly allows the controller to differentiate the received localization signals with respect to their origin. This allows for a much easier and accurate determination of the position and/or orientation of the additional coil.

In an embodiment, the localizer further comprises a motion model provider adapted to provide a motion model which is indicative of a movement of a region of interest to which the additional coil is attached, and the processor is adapted to determine a current position and/or orientation of the additional coil further based on the motion model. The motion model provider can refer to a storage unit for storing one or more motion models, wherein the motion model provider can then provide the stored one or more motion models. The motion model provider can also be in communication with a storage unit storing one or more motion models or with a device generating a motion model, wherein the motion model provider can then receive the one or more motion models for providing the same. The storage unit may be any sort of memory device, computer drive (e.g., solid state drive such as a FLASH drive), optical disk, etc. The provided motion model is indicative of a movement of a region of interest to which the additional coil is attached. For example, if the additional coil is used in an interventional procedure, the additional coil may be attached to a chest of a human being, wherein in this case the motion model can be indicative of a movement of a chest region of a human being. However, in other applications the additional coil can be attached to other regions of interest and the motion model can then be provided such that it is indicative of a respective movement of this region of interest. The motion model provider can, for instance, be adapted to select a motion model from a plurality of motion models each referring to a different region of interest based on knowledge of the region of interest to which the additional coil is attached. For example, a user can provide an input indicative of a region of interest to which the additional coil is attached, and the motion model provider can then be adapted to select and provide a motion model that is associated with this region of interest.

The motion model can be indicative, for instance, of a 1D, 2D or even 3D movement of the region of interest, for instance, based on measurements of the movement of the region of interest, or simulations of the movement of the region of interest. For example, the motion model can be provided as a video stream from a camera monitoring a region of interest, as a breathing signal indicating the movement of a chest region, as an EEG signal indicative of a heart movement, as a spline model for different movement phases of the region of interest, etc. Generally, the motion model provides an indication of where in a space the region of interest is located with respect to time. The processor can utilize this information for determining a current position and/or orientation of the additional coil. In particular, the processor can be adapted to use an estimation from the motion model indicating where the additional coil is currently positioned and/or oriented as a starting point for the algorithm for determining the current position and/or orientation based on the sensitivity information and the received localization signal. This allows for a much faster and more accurate determination of the position and/or orientation of the additional coil. However, the processor can also be adapted to utilize an expected position and/or orientation of the additional coil derived from the motion model to verify a position and/or orientation determined based on the sensitivity information and the received localization signal. This allows, for instance, to easily select a correct solution for the position and/or orientation of the additional coil when more than one solution is provided by the algorithm determining the position and/orientation of the additional coil based on the sensitivity information and the localization signal. Moreover, after having once determined a current position and/or orientation of the additional coil, for instance, based on the sensitivity information, the received localization signal and optionally on the motion model, the processor can also be adapted to utilize the motion model to extrapolate a position and/or orientation of the additional coil for time periods during which no electromagnetic localization signal is sent, for instance, if the electromagnetic localization signal is not sent continuously. This allows for an accurate tracking of the position and/or orientation of the additional coil even in embodiments in which no continuous electromagnetic localization signal is present.

In an embodiment, the additional coil further comprises an accelerometer adapted for measuring an acceleration of the additional coil, and the processor is adapted to determine a current position and/or orientation of the additional coil further based on the measured acceleration of the additional coil. The accelerometer can be any known accelerometer providing measurements of the acceleration in one or more directions. For instance, the accelerometer can refer to a single or multi-axis accelerometer that is adapted to measure both the magnitude and the direction of an acceleration of the additional coil. Moreover, the accelerometer can comprise or refer also to an angular accelerometer and/or an angular rate sensor, like a gyroscope, to measure a rotational acceleration. In a beneficial embodiment, the accelerometer refers to a micro-electromagnetic system accelerometer. As already explained above with respect to providing a motion model, also an acceleration measurement provides information indicative of the movement of the additional coil and accordingly allows determination of a position and/or orientation of the additional coil more accurately. For example, the processor can be adapted, after a first position of the additional coil is determined, for instance, based on the sensing information and the received localization signal, to use the measured acceleration to determine a current position and/or orientation of the additional coil, for example, in cases in which no continuous electromagnetic localization signal is present. Moreover, the measured acceleration also allows for determining an expected position and/or orientation of the additional coil, wherein the processor can be adapted to then use this expected position and/or orientation as a starting point for an algorithm determining the position and/or orientation of the additional coil based on the sensitivity information and the received localization signal. Moreover, the processor can also be adapted to regard the acceleration measurements as a motion model or can be adapted to utilize the acceleration measurements for generating a motion model that is indicative of the movement of the additional coil. The processor can then utilize the motion model as already described above. Generally, also in this embodiment the providing of an additional accelerometer allows for a more accurate determination of a current position and/or orientation of the additional coil and hence to a more accurate determination of the location of the magneto-mechanical oscillator.

In a beneficial embodiment, the processor is further adapted to determine whether a measured acceleration lies above a predetermined acceleration threshold, wherein if the measured acceleration lies above the predetermined acceleration threshold, the controller can be adapted to control the coil, i.e. the main sending coil and/or the additional coil, respectively, to again send an electromagnetic localization signal. In particular, it can be expected that if the measured acceleration exceeds the predetermined acceleration threshold that the additional coil has changed its position and/or orientation in a manner that might be difficult to determine simply based on the measured acceleration, so that for an accurate position and/or orientation determination it will be advantageous to again perform the localization of the additional coil based on the electromagnetic localization signal. The predetermined acceleration threshold can be predetermined, for instance, based on an experience of a user of the system or can generally refer to an acceleration value that is known to indicate a positional change outside of some safety margin that might be provided by a user depending on the application of the additional coil. Moreover, in an embodiment, the processor can be adapted to integrate the acceleration signal once, resulting in a velocity signal, and/or integrate the acceleration signal twice, resulting in a position signal. Based on these integration results, also thresholds can be determined as described above for determining whether a new determination of the position and/or orientation is necessary by, for example, again performing the localization of the additional coil based on the electromagnetic localization signal.

In an embodiment, the system comprises more than one additional coil, wherein the processor is adapted to determine the positions and/or orientations of the additional coils sequentially by utilizing already determined positions and/or orientations of the additional coils. In this embodiment the system comprises an additional coil array with, beneficially, at least two additional coils. Determining the positions and/or orientations of the additional coils sequentially by utilizing already determined positions and/or orientations of the additional coils allows for a more accurate determination of the positions and/or orientations of all the additional coils. In a beneficial example, the processor is adapted to use a computational model that allows it to model signals sent and received by the main coils, i.e. the main receiving coil and the main sending coil, and further sent and/or received by the additional coils. Employing this computational model, the processor can be adapted to modify the ascertained position and/or orientation of a first additional coil until the virtual received localization signals modelled by the computational model are optimized with respect to the actually measured received localization signals. The corresponding position and/or orientation of the first additional coil is then fixed in the computational model relative to the positions and/or orientations of the main coils. With this updated computational model, the next additional coil is then processed in in a similar manner, then the third, etc., until all additional coils are processed. Based on the positions and/or orientations determined during this process, the computational model can then again be applied to the first coil, and so on. This could be repeated until a difference between the computed received localization signals and the actually measured received localization signals is below a predetermined threshold, e.g., is minimized, leading to an iterative determination of the positions and/or orientations of all additional coils.

In an embodiment, the electromagnetic localization signal has an amplitude that does not saturate a receiving circuitry of the additional coil and/or of the main receiving coil, respectively, wherein the receiving circuitry is adapted to generate the received localization signal based on the received electromagnetic localization signal. Generally, it is known that any receiving circuitry comprises a saturation threshold above which a generated received localization signal is not indicative of an amplitude of the received electromagnetic localization signal any more. Accordingly, it is beneficial to avoid a saturation of the receiving circuitry of the additional coil and/or of the main receiving coil, respectively. Accordingly, the controller can be adapted to control the main sending coil and/or the additional coil to send an electromagnetic localization signal that has an amplitude which is known does not saturate the receiving circuitry of the additional coil and/or the main receiving coil, respectively. However, as already explained above, a saturation of a receiving circuitry can also be avoided by adapting the receiving circuitry appropriately.

In an embodiment, the electromagnetic localization signal refers to a signal having signal characteristics that lie outside of a signal characteristic range utilized for the excitation of the magneto-mechanical oscillator. Accordingly, the electromagnetic localization signal does not refer to the electromagnetic excitation signal utilized for exciting the magneto-mechanical oscillator. The signal characteristics can refer to any characteristic of the signal, for instance, to a frequency, an amplitude, a pulse sequence, etc. Beneficially, the electromagnetic localization signal comprises a frequency different from the frequency of the electromagnetic excitation signal. Generally, it is beneficial that the electromagnetic localization signal is provided such that it allows for a computational modelling of the received localization signal based on a computational model of the main coil array and the additional coil. In this case it is beneficial that the electromagnetic localization signal comprises a frequency or frequency range that does not lead to an influence of the patient on the localization signal. Beneficially, the frequency or frequency range of the electromagnetic localization signal is below 10 MHz, more beneficially below 1 MHz, and even more beneficially below 100 kHz. The processor is then beneficially adapted to model the computed received localization signal and to compare this signal with the measured and received localization signal, for instance, by subtracting the optionally respectively scaled, computed received localization signal from the actually measured received localization signal in order to determine the position and/or orientation of the additional coil. In this embodiment, but also in other embodiments, the processor can also be adapted to take an influence of the patient on the electromagnetic localization signal into account during the determination of the position and/or orientation of the additional coil, for example, in the same way as described above with respect to a magnetic or magnetizable object.

In an alternative embodiment, the electromagnetic localization signal can also refer to the electromagnetic excitation signal. This allows in particular an accurate determination of the position and/or orientation of the additional coil for all time periods in which also the magneto-mechanical oscillator is excited and thus for which the localization of the magneto-mechanical oscillator shall be determined. Accordingly, the position and/or orientation of the additional coil is only determined when necessary.

In an embodiment, the additional coil comprises a local energy storage element or device, for instance, a battery. This embodiment has the advantage that the additional coil does not have to be provided with a wired connection to a power source that might be inconvenient in an area of interest, for instance, during an interventional procedure. In a beneficial embodiment, the additional coil comprises a local energy storage element which is adapted to be charged by an electromagnetic charge signal. and the controller is adapted to control the sending coil to send an electromagnetic charge signal to the additional coil that is adapted to charge the local energy storage element of the additional coil. In this embodiment, strong batteries that might increase a size or weight of the additional coil can be avoided. Instead, the local energy storage element can comprise a battery with only a short battery life, for instance, of a few minutes, wherein after this time the controller is adapted to control the main sending coil to send the electromagnetic charge signal to again charge the battery. In a beneficial embodiment, the electromagnetic charge signal refers to the electromagnetic localization signal such that during the localization process also the local energy storage element can be charged. Generally, methods for charging an energy storage element without utilizing a wired connection, i.e. by utilizing electromagnetic signals, are known in the art. However, in another embodiment, the additional coil can also comprise a local energy storage element, like a battery, that is not charged by additional electromagnetic signals.

It may be beneficial that, if the additional coil comprises a local energy storage element and thus no wired connection to a power source, also the received signals, i.e. the electric signals indicative of the received electromagnetic signals, are provided to the localizer utilizing a wireless connection. For example, Bluetooth, WiFi, or any other known wireless communication can be utilized. Moreover, also for sending an electromagnetic signal the additional coil can be wirelessly connected to the localizer or any other controller adapted to control a sending of a signal for the additional coil.

Moreover, when the additional coil comprises a local energy storage element like a battery, it is beneficial that the additional coil is adapted to provide a sleep mode in which the additional coil consumes less energy than in the normal mode, beneficially substantially no energy. The controller can then be adapted to control the additional coil to go into the sleep mode if it is currently not used during its application, i.e. if currently no electromagnetic signals are provided that shall be received by the additional coil. The controller can then also be adapted to wake up the additional coil, i.e. to end the sleep mode and change into the normal operation mode. However, the additional coil can also comprise a sleep mode circuitry that is adapted to control the additional coil to change between the sleep mode and the normal mode. For example, the sleep mode circuitry can be adapted to react based on the receiving of a predetermined signal to change from the normal operation mode to the sleep mode or to change from the sleep mode to the normal operation mode. The controller can then be adapted to control the main sending coil to send the respective predetermined signal to the additional coil. However, the sleep mode circuitry can also be adapted to automatically change from the normal operation mode to the sleep mode, for instance, if for a predetermined time period no electromagnetic localization signal or response signal has been received by the additional coil.

In an embodiment, the additional coil comprises an LC circuit, wherein the resonance frequency of the LC circuit lies in the frequency range of the electromagnetic excitation signal of the magneto-mechanical oscillator. Generally, an LC circuit consists of an inductor and a capacitor that are connected to each other. Such an LC circuit can thus act as an electrical resonator with a predetermined resonance frequency. If an LC circuit is positioned as part of the additional coil near the magneto-mechanical oscillator, the LC circuit provides an amplification of the electromagnetic excitation signal in the vicinity of the magneto-mechanical oscillator which leads to an increased excitation of the magneto-mechanical oscillator. Such an increase in the excitation of the magneto-mechanical oscillator also leads to a stronger signal provided by the magneto-mechanical oscillator which allows for a much easier localization of the magneto-mechanical oscillator. Moreover, this signal provided by the excitation of the magneto-mechanical oscillator can again be amplified by the LC circuit and provide an even stronger signal. The system can then further comprise an LC circuit location provider that is adapted to provide a location of the LC circuit. For example, the location of the LC circuit can be fixed in relation to the additional coil such that the location of the LC circuit can be provided in relation to the position and/or orientation of the additional coil or based on a known position and/or orientation of the additional coil. However, the system can also be adapted to determine the position of the LC circuit, for instance, using the same approaches, as discussed above with respect to the localization of the additional coil. The localization of the magneto-mechanical oscillator can then be further based on the known location of the LC circuit. Beneficially, the additional coil refers to the inductor of the LC circuit such that by providing a capacitor in connection with the additional coil the capacitor together with the additional coil forms the LC circuit. Optionally, an additional inductor can be provided in the LC circuitry, and beneficially it may comprise a soft magnetic core. This can increase the quality factor of the LC circuitry. Beneficially, the LC circuitry can also be used together with a local energy storage element for maximizing the energy transferred to the local energy storage element. However, since as already described above the presence of an LC circuitry can influence the electromagnetic signals sent and/or received by the additional coil, it is beneficial that the controller is adapted to control the additional coil such that the LC circuitry is only utilized during an energy transfer and, beneficially, not during a localization of the additional coil and/or the magneto-mechanical oscillator.

In a further aspect of the invention, a medical coil system for receiving signals from a magneto-mechanical oscillator is presented, wherein the medical coil system is adapted to be used in a medical application, wherein the medical coil system comprises a) a main coil array comprising a main receiving coil adapted to receive an electromagnetic response signal of the magneto-mechanical oscillator and a main sending coil adapted to send an electromagnetic excitation signal for exciting the magneto-mechanical oscillator, and b) an additional coil adapted to receive an electromagnetic response signal of the magneto-mechanical oscillator and/or to send an electromagnetic excitation signal for exciting the magneto-mechanical oscillator. In particular, the medical coil system is adapted to be controlled and used together with a localizer, as described above. Moreover, the coils of the medical coil system, i.e. the main coils and the additional coil, can be adapted, as described above, with respect to the system for receiving an electromagnetic response signal of the magneto-mechanical oscillator. Accordingly, the medical coil system can be regarded as a part of the system described above.

In a further aspect of the invention, a localizer is presented, wherein the localizer is adapted to be used together with a main coil array comprising a main receiving coil adapted to receive an electromagnetic response signal of the magneto-mechanical oscillator and a main sending coil adapted to send an electromagnetic excitation signal for exciting the magneto-mechanical oscillator, and an additional coil adapted to receive an electromagnetic response signal of the magneto-mechanical oscillator, wherein the localizer is adapted to localize the additional coil, wherein the localizer comprises i) a controller adapted a) to control the main sending coil to send an electromagnetic localization signal that is receivable by the additional coil and to control the additional coil to generate a received localization signal indicative of the electromagnetic localization signal received by the additional coil, and/or b) to control the additional coil to send an electromagnetic localization signal that is receivable by the main receiving coil and to control the main receiving coil to generate a received localization signal indicative of the electromagnetic localization signal received by the main receiving coil, ii) a sensitivity provider adapted to provide a sensitivity information that is indicative of a sensitivity profile of a) the additional coil and the main sending coil, respectively, if the main sending coil is controlled to send the electromagnetic localization signal, and/or b) the additional coil and the main receiving coil, respectively, if the additional coil is controlled to send the electromagnetic localization signal, and iii) a processor adapted to determine a position and/or orientation of the additional coil based on the provided sensitivity information and based on the received localization signal.

In a further aspect of the invention, a method is presented for being used with a main coil array comprising a main receiving coil adapted to receive an electromagnetic response signal of the magneto-mechanical oscillator and a main sending coil adapted to send an electromagnetic excitation signal for exciting the magneto-mechanical oscillator, and an additional coil adapted to receive an electromagnetic response signal of the magneto-mechanical oscillator, are presented, wherein the localizer is adapted to localize the additional coil, wherein the method comprises i) controlling a) the main sending coil to send an electromagnetic localization signal that is receivable by the additional coil and the additional coil to generate a received localization signal indicative of the electromagnetic localization signal received by the additional coil, and/or b) the additional coil to send an electromagnetic localization signal that is receivable by the main receiving coil and the main receiving coil to generate a received localization signal indicative of the electromagnetic localization signal received by the main receiving coil, ii) providing a sensitivity information that is indicative of a sensitivity profile of a) the additional coil and the main sending coil, respectively, if the main sending coil is controlled to send the electromagnetic localization signal, and/or b) the additional coil and the main receiving coil, respectively, if the additional coil is controlled to send the electromagnetic localization signal, and iii) determining a position and/or orientation of the additional coil based on the provided sensitivity information, and based on the received localization signal.

In a further aspect of the invention, a computer program product for determining a location of a coil is presented, wherein the computer program product comprises a non-transitory, tangible, medium having stored thereon program code for causing a processor of the localizer as described herein to execute one or more methods as described herein.

A still further aspect of the invention provides a kit for use with an existing system which comprises a main coil array, wherein the main coil array comprises a main receiving coil which is configured to receive an electromagnetic response signal of a magneto-mechanical oscillator, and wherein the main coil array further comprises a main sending coil which is configured to transmit an electromagnetic excitation signal for exciting the magneto-mechanical oscillator. The kit comprises at least one moveable additional coil which is configured to be placed in a region of interest with respect to the magneto-mechanical oscillator and is configured to transmit an additional electromagnetic excitation signal for exciting the magneto-mechanical oscillator and/or receive the electromagnetic response signal of a magneto-mechanical oscillator. The kit further comprises at least one non-transitory, tangible, medium having stored thereon program code which is executable to cause at least one of the main sending coil and the at least one moveable additional coil to transmit an electromagnetic localization signal, and to provide from at least one of the at least one moveable additional coil and the main receiving coil a received localization signal, and is further executable for causing a processor to locate at least one of a position and an orientation of the at least one moveable additional coil from the received localization signal.

In some embodiments, the electromagnetic localization signal is a pilot tone signal.

In some embodiments, the at least one non-transitory, tangible, medium may have further stored thereon information about one or more construction properties of the at least one moveable additional coil, wherein the one or more construction properties include at least one of a diameter and a number of windings of the at least one moveable additional coil.

In some embodiments, the program code may be further configured to cause the processor to determine sensitivity information of the at least one additional coil for the electromagnetic response signal based at least in part on the one or more construction properties of the at least one moveable additional coil and further based on the at least one position and orientation of the at least one moveable additional coil.

In some embodiments, the electromagnetic excitation signal is transmitted repeatedly and the program code is executable to cause the electromagnetic localization signal to be transmitted repeatedly, prior to the repeated transmissions of the electromagnetic excitation signal.

It shall be understood that the system as described above, the coil system as described above, the localizer as described above, the method as described above, the computer program as described above, and the kit as described above may have similar and/or identical preferred embodiments, in particular, as defined in the dependent claims.

It shall be understood that embodiments of the present invention can also be produced by any combination of the features in dependent claims, or above embodiments, with the respective independent claim.

These and other aspects of the invention will be apparent from and elucidated with reference to the embodiments described hereinafter.

DETAILED DESCRIPTION OF EMBODIMENTS

Figure 1:
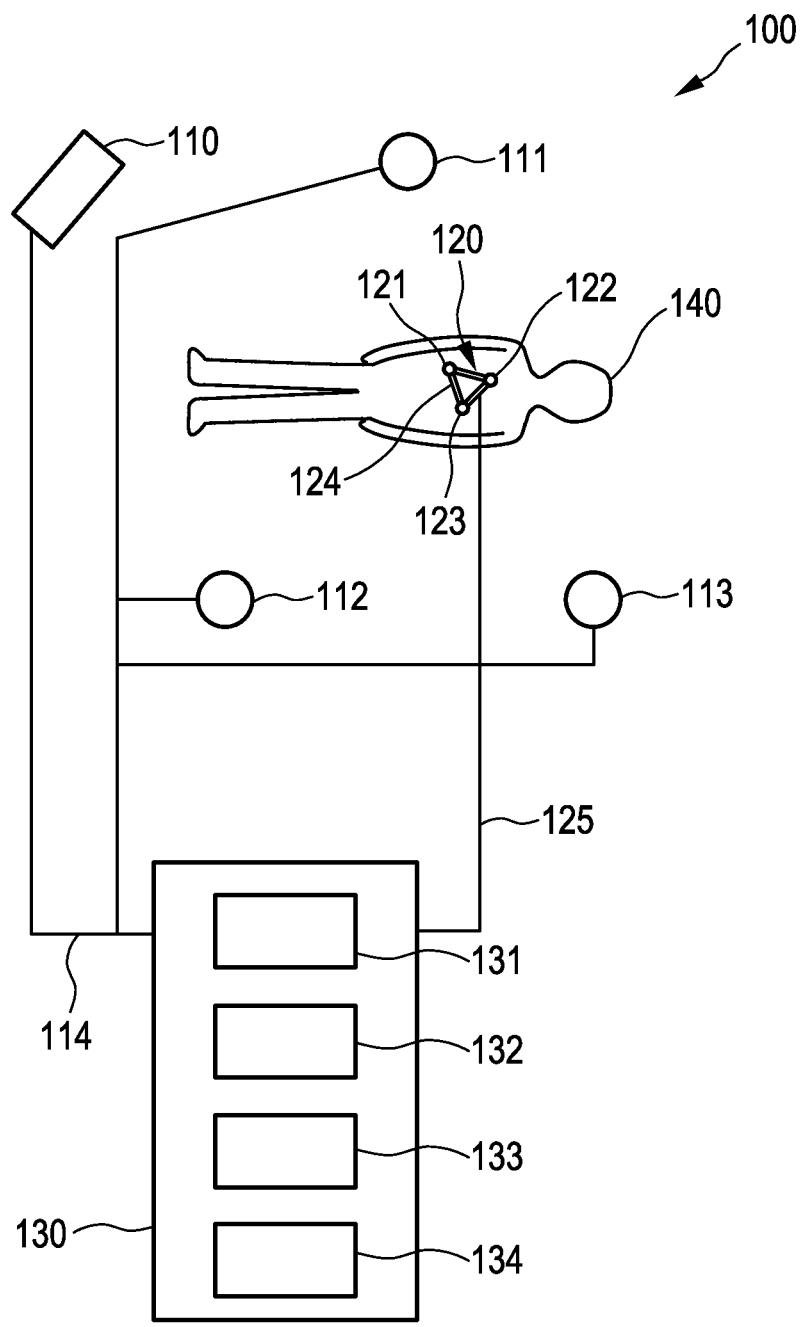
FIG. 1 shows schematically and exemplarily an embodiment of a system for localizing a magneto-mechanical oscillator.

FIG. 1 shows schematically and exemplarily an embodiment of a system 100 for receiving signals from a magneto-mechanical oscillator. In the example shown in FIG. 1, the system 100 is applied in an interventional procedure in which a magneto-mechanical oscillator, not shown in FIG. 1, is used inside a patient 140, for instance, for localizing an interventional device, like a catheter or needle. The system 100 comprises a main coil array comprising, in this example, a main receiving coil array with main receiving coils 111, 112, 113, and a main sending coil 110. The main sending coil 110 is adapted to send an electromagnetic excitation signal for exciting the magneto-mechanical oscillator provided within the patient 140. The main receiving coils 111, 112, 113 of the main receiving coil array are adapted to receive an electromagnetic response signal provided by the excited magneto-mechanical oscillator. Based on the signals of the magneto-mechanical oscillator received by the main receiving coils 111, 112, 113, a location of the magneto-mechanical oscillator within the patient 140 can be determined. Moreover, the electromagnetic response signals of the magneto-mechanical oscillator can further be encoded with additional information, for instance, identification information of the magneto-mechanical oscillator or sensing information indicative of a physical parameter sensed in the environment of the magneto-mechanical oscillator, wherein also this further information can be determined using the electromagnetic response signal of the magneto-mechanical oscillator received by the main receiving coils 111, 112, 113.

The main coils 110, 111, 112, 113 of the main coil array can, for example, refer to planar coils with a diameter of 10 cm to 20 cm and which are made from aluminum, wherein the main coils 110, 111, 112, 113 may comprise an inductance smaller than 200 µH. Such small inductances allow an operating voltage to be kept small, which allows also keeping the isolation requirements for the coils small. However, also other realizations of the main coils 110, 111, 112, 113 can be suitable based on the intended application of the main coil array.

In order to allow for a more accurate receiving of the signals from the magneto-mechanical oscillator during the interventional procedure, an additional (moveable) coil array 120 can be provided as part of the system 100 in a region of interest of the patient 140. In this example, the additional (moveable) coil array 120 comprises additional coils 121, 122, 123 which, as part of the moveable coil array can also be considered to be moveable coils, and which may be arranged on a chest of the patient 140. Also the additional coils 121, 122, 123 of the additional (moveable) coil array 120 are adapted to receive an electromagnetic response signal of the magneto-mechanical oscillator and/or are adapted to send an electromagnetic excitation signal for exciting the magneto-mechanical oscillator provided within the patient 140. In the example shown in FIG. 1, the additional coils 121, 122, 123 are arranged on a mounting support 124 that can be used for attaching the additional (moveable) coil array 120 on the area of interest of the patient 140. In particular, the mounting support 124 allows to arrange the additional coils 121, 122, 123 in a known spatial relation to each other, for instance, a spatial relation determined by the structure of the mounting support 124. However, in other embodiments the mounting support 124 can be omitted and the additional coils 121, 122, 123 may be individual moveable coils which can be freely placed, for instance, by a physician performing the interventional procedure, in the region of interest of the patient 140.

The additional coils 121, 122, 123 of the additional coil array 120 can, for example, also refer to planar coils made from aluminum. The diameter of the additional coils 121, 122, 123 is beneficially smaller than the diameter of the main coils 110, 111, 112, 113 and the additional coils 121, 122, 123 can also comprise an inductance smaller than 200 µH. However, also other realizations of the additional coils 121, 122, 123 can be suitable based on the intended application of the additional coil array. In particular, the system 100 can comprise different additional coils for different medical applications. In particular, different additional coils with a diameter adapted to a maximal distance between a respective additional coil and the magneto-mechanical oscillator expected for a respective medical application can be provided.

Further, the system 100 comprises a localizer 130 that is adapted to localize the additional coils 121, 122, 123 of the additional coil array 120. The localizer can be implemented as part of the hardware and/or software of any known computing device. For instance, the localizer 130 can be provided as a standalone device or as part of the hardware and/or software of a computing device providing also other functionalities. Beneficially, the localizer 130 may be provided as part of the hardware and/or software of a computing device that is already used for determining the location of the magneto-mechanical oscillator based on the electromagnetic response signals of the excited magneto-mechanical oscillator received by the main coil array and the additional coil array 120. The localizer 130 can be wired or wirelessly connected to the main coil array and the additional coil array 120 as indicated by the connecting lines 114 and 125. The localizer 130 comprises a sensitivity provider 131, a controller 132, optionally a motion model provider 133 and a processor 134.

The sensitivity provider 131 is adapted to provide sensitivity information that is indicative of the sensitivity profile of the additional coils 121, 122, 123 and/or of the main receiving coils 111, 112, 113 and/or of the main sending coil 110. In particular, the sensitivity provider 131 is adapted to provide the sensitivity information that is necessary for determining the position and/or orientation of the additional coils 121, 122, 123. Since generally sensitivity information that is indicative of sensitivity profiles of all coils involved in the sending and receiving of the electromagnetic localization signal is taken into account, it is beneficial that the sensitivity provider 131 is adapted to provide the respective sensitivity information such that it is indicative of the sensitivity profiles of the respective involved coils. For example, if the main sending coil 110 is controlled to send the electromagnetic localization signal and the additional coils 121, 122, 123 are controlled to receive the electromagnetic localization signal, the sensitivity provider 131 is adapted to provide the sensitivity information to be indicative of the sensitivity profiles of the main sending coil 110 and the additional coils 121, 122, 123. Generally, it is beneficial that the sensitivity information for each of the coils 110, 111, 112, 113, 121, 122, 123 is already known and, for instance, stored on a storage unit, such as any type of memory device, computer drive (e.g., a solid state drive such as a FLASH drive), optical disk, remote server, etc. The sensitivity provider 131 can then be adapted to select the respective sensitivity information from the storage unit. The sensitivity information of these coils 110, 111, 112, 113, 121, 122, 123 can, for instance, be determined during a calibration procedure of the system 100 before the interventional procedure or can be provided, for instance, by a manufacturer of the system 100. For example, the sensitivity profiles of each of the coils can be determined by utilizing a virtual simulation model optionally in combination with actual measurements of the magnetic field of the coils. The simulation model can be provided by virtually providing the conductors of the respective coil in the simulation model and then utilizing the Biot-Savart law to simulate the magnetic field of the virtual coil conductors. To calibrate and/or verify the simulated magnetic field, optionally measurements of the magnetic field, in particular, of the flux density of the magnetic field, can be performed at some locations around the actual coil. These measurements can then be utilized for calibrating the simulation model of the coil such that the simulated magnetic field corresponds to the actually measured magnetic field at the respective locations. This allows the accuracy of the simulation model to be improved and to take into account, for instance, deviations of the actual coil from the specification that might be due to production inaccuracies. However, also other known methods for determining a sensitivity profile of the coils can be utilized for providing the sensitivity information. The sensitivity information can then refer to the respective sensitivity profile itself or can refer to other measures of the sensitivity profile. For instance, the sensitivity information can refer to the simulation model of the coil, in particular, to the positions and orientations of the virtual conductors in the simulation model, since from these the sensitivity profiles can directly be derived using known physical laws.

The controller 132 can then be adapted to control the main sending coil 110 to send an electromagnetic localization signal that can be received by the additional coils 121, 122, 123 and further to control the additional coils 121, 122, 123 to generate a received localization signal indicative of the electromagnetic localization signal received by the additional coils 121, 122, 123. Additionally or alternatively, the controller can also be adapted to control the additional coils 121, 122, 123 to send an electromagnetic localization signal that can then be received by the main receiving coils 111, 112, 113 and to control the main receiving coils 111, 112, 113 to generate a received localization signal indicative of the electromagnetic localization signal received by the main receiving coils 111, 112, 113. Generally, the received localization signal can refer to an electric signal that is generated by a receiving circuitry provided as part of each of the additional coils 121, 122, 123 or as part of the main receiving coils 111, 112, 113, respectively. Beneficially, the additional coils 121, 122, 123 are provided with a receiving circuitry that is adapted such that a saturation threshold for the receiving circuitry is not reached when the additional coils 121, 122, 123 receive the electromagnetic excitation signal sent by the main sending coil 110. Such a receiving circuitry can, for instance, be realized by providing a respective damping mechanism comprising, for instance, a damping element, that allows for a damping of the received signals in the receiving circuitry such that also for the electromagnetic excitation signal sent by the main sending coil 110 each of the additional coils 121, 122, 123 can generate a received localization signal that is indicative of the amplitudes of the received electromagnetic localization signal. A more detailed example of such a receiving circuitry will be described with respect to FIG. 3.

The processor 134 is then adapted to determine a position and/or orientation of the additional coils 121, 122, 123 of the additional coil array 120 based on the provided sensitivity information of the additional coils 121, 122, 123 and the main sending coil 110 and the received localization signal, if the received localization signal is generated by the additional coils 121, 122, 123. In a case in which the received localization signal is generated by the main receiving coils 111, 112, 113, the processor is adapted to determine the position and/or orientation of the additional coils 121, 122, 123 based on the sensitivity information of the main receiving coils 111, 112, 113 and the additional coils 121, 122, 123. Generally, the determination of the position and/or orientation of the additional coils 121, 122, 123 can be based on known coil localization algorithms and/or on algorithms similar to the algorithms used for localizing the magnetomechanical oscillator. For example, in a beneficial embodiment, a computational model is provided for determining the positions and/or orientations of the additional coils 121, 122, 123. Beneficially, the processor 134 is adapted to apply a computational model that incorporates the sensitivity information, for example, provided in the form of the positions and/or orientations of all conductors that can represent a magnetic field of the coil generated by the respective coil when provided with a known current. However, the sensitivity information can also be directly included into the computational model as sensitivity profiles of the respective coils. Based on the sensitivity information incorporated into the computational model of the coils and based on the known physical laws, virtually received localization signals can be simulated in dependency of the relative position and/or orientation of the coils involved in the localization process. Optionally, to increase the accuracy of the computational model, further influences can be taken into account. For example, the sending and/or receiving circuitry of the respective coils can also be incorporated into the computational model and its/their effects on the virtual received localization signal can be simulated. The simulated received localization signal can then be compared with the actually measured received localization signal. By varying the relative positions and/or orientations of the coils involved, in the computational model, the relative positions and/or orientations of the respective coils that minimize the difference between the virtual received localization signal and the measured received localization signal can then be determined as the actual positions and/or orientations of the respective coils. Accordingly, the determining of the positions and/or orientations of the respective coils can be regarded as an optimization problem and can be solved using known optimization algorithms, for instance, iterative or direct solvers. If information on the positions and/or orientations of the respective coils, for instance, of the main coils and/or the additional coils, is already available, this location information can further be taken into account in the computational model, for instance, as starting point for the optimization process. In order to further increase the accuracy of the computational model and the optimization process, further influences on the received localization signal can be taken into account, in particular, influences that lead to deviations from an expected received localization signal. Beneficially, influences on the accuracy of the received localization signal are taken into account as an error function. For example, for some commonly used amplifiers the actual amplification is within certain error boundaries and therefore not exactly predictable. Accordingly, a certain error has to be taken into account that can be caused by such an amplifier. All identified influences on an expected error of the received localization signal can then be provided in the form of an error function together with respective weights that can be used to weight the influences of each of the terms of the error function. The error function can then be incorporated into the optimization process using known methods and algorithms. The result of the optimization is then provided by the processor 134 as the position and/or orientation of the additional coils, and optionally, if not already known, also of the main coils. Generally, also other known algorithms can be used that allow the processor 134 to determine the position and/or orientation of electromagnetic signal sources.

Beneficially, in embodiments in which more than one additional coil is provided as shown in the embodiment of FIG. 1, it is beneficial that the position and/or orientation of each additional coil 121, 122, 123 is subsequently determined by the processor 134 based respectively on already known positions and/or orientations of at least one of the additional coils 121, 122, 123. Moreover, in the embodiment shown in FIG. 1, the known spatial relation between the additional coils 121, 122, 123 provided by the mounting support 124 can advantageously be utilized by the processor 134 for determining the position and/or orientation of the additional coils 121, 122, 123. For example, the processor 134 can be adapted to determine first the position and/or orientation of only one of the additional coils, for instance, of the additional coil 121, based on the sensitivity information and the received localization signal and to determine the further positions and/or orientations of the additional coils 122, 123 based on the known spatial relation of these additional coils to the position and/or orientation of the additional coil 121. However, the processor 134 can also be adapted to utilize the spatial information provided by the mounting support 124 in other ways, for instance, for verifying a result of the position and/or orientation determination based on the sensitivity profiles and the received localization signals, or, as mentioned above, as starting point for an optimization algorithm.

In a beneficial embodiment, the localizer 130 further comprises a motion model provider 133. The motion model provider 133 can be adapted to provide a motion model of a region of interest to which the additional coil array 120 is attached. In the case shown in FIG. 1, the additional coil array 120 is attached to a chest of a patient 140. Accordingly, in this case the motion model provider 133 can be adapted to provide a motion model of a chest of a human being. Generally, the motion model provided by the motion model provider 133 can be a general motion model of the region of interest. For example, in the case shown in FIG. 1 it can be a general model of a chest motion of a human being that might have been acquired by averaging the chest movement measured from different persons. However, the provided motion model can also be a specific motion model, in particular, a motion model specific for the patient 140. For example, in the embodiment shown in FIG. 1, the motion model can refer to a motion model that is specific for the patient 140 and might have been determined based on measuring a past or current chest motion of the patient 140. In a beneficial embodiment, a motion sensor is attached to the region of interest of the patient 140, in FIG. 1 the chest of the patient 140, and the measurement signal provided by the motion sensor is directly utilized as a motion model and provided by the motion model provider 133.

If a motion model is provided by the motion model provider 133, the processor 134 can be adapted to determine the position and/or orientation of the additional coils 121, 122, 123 further based on the motion model. In particular, the processor 134 can be adapted to estimate a current position and/or orientation of the additional coils 121, 122, 123 based on the motion model and then utilize this estimated position and/or orientation as a starting point for an algorithm for determining the current position and/or orientation of the additional coils 121, 122, 123, for instance, as described above, as a starting point in the computational model. However, the processor 134 can also be adapted to utilize the motion model to estimate a position and/or orientation of the additional coils 121, 122, 123 during time periods in which no electromagnetic localization signal is provided for localizing the additional coils 121, 122, 123. Accordingly, based on the motion model the current position of the additional coils 121, 122, 123 can be tracked accurately even if no continuous electromagnetic localization signal can be provided.

After the position and/or orientation of the additional coils 121, 122, 123 has been determined, the determined positions and/or orientations can be utilized in an algorithm for determining, for instance, a location of the magneto-mechanical oscillator during the interventional procedure. Moreover, the processor 134 can be adapted to provide the determined positions and/or orientations to a user of the system 100, for example, a physician, for example via a display device. This allows for a verification of the result. Moreover, the determined positions and/or orientations can be incorporated into a framework of the medical procedure, for instance, can be shown on a display in relation to an anatomical image of the patient 140 such that the additional coils 121, 122, 123 can also be utilized as markers on the patient 140. For example, a movement of the region of interest of the patient 140 can also be derived from changes in the positions and/or orientations of the additional coils 121, 122, 123.

Figure 2:
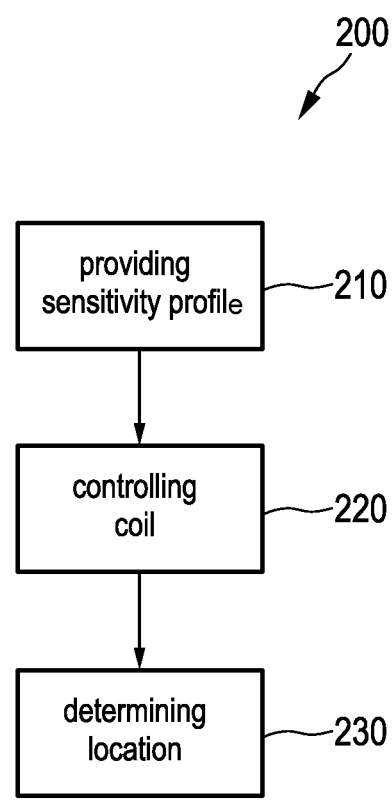
FIG. 2 shows schematically and exemplarily a flow chart of a method for determining a location of an additional coil of the system.

FIG. 2 shows schematically and exemplarily a method for localizing an additional coil in a system like system 100 shown in FIG. 1. In particular, the method 200 comprises a first operation 210 of providing sensitivity information of the additional coils 121, 122, 123 and/or of the main receiving coils 111, 112, 113 and/or of the main sending coil 110, as described above. In a further operation 220, the method 200 can comprise controlling the main sending coil 110 to send an electromagnetic localization signal that can be received by the additional coils 121, 122, 123, and controlling the additional coils 121, 122, 123 to generate a received localization signal indicative of the electromagnetic localization signal received by the additional coils 121, 122, 123. Additionally or alternatively, in the operation 220 the method 200 can also comprise controlling the additional coils 121, 122, 123 to send an electromagnetic localization signal that can be received by the main receiving coils 111, 112, 113, and controlling the main receiving coils 111, 112, 113 to generate a received localization signal indicative of the electromagnetic localization signal received by the main receiving coils 111, 112, 113. Generally, the operations 210 and 220 can be performed in any order or even at the same time. Further, the method 200 comprises an operation 230 of determining a position and/or orientation of the additional coils 121, 122, 123 based on the sensitivity information of the additional coils 121, 122, 123 and the main sending coil 110 and based on the received localization signals, if the received localization signals are generated by the additional coils 121, 122, 123. Additionally or alternatively, the operation 230 can comprise determining a position and/or orientation of the additional coils 121, 122, 123 based on the sensitivity information of the main receiving coils 111, 112, 113 and the additional coils 121, 122, 123 and based on the received localization signals, if the received localization signals are generated by the main receiving coils 111, 112, 113. Generally, the position and/or orientation of the additional coils 121, 122, 123 can be determined in accordance with any of the principles described above with respect to FIG. 1.

Figure 3:
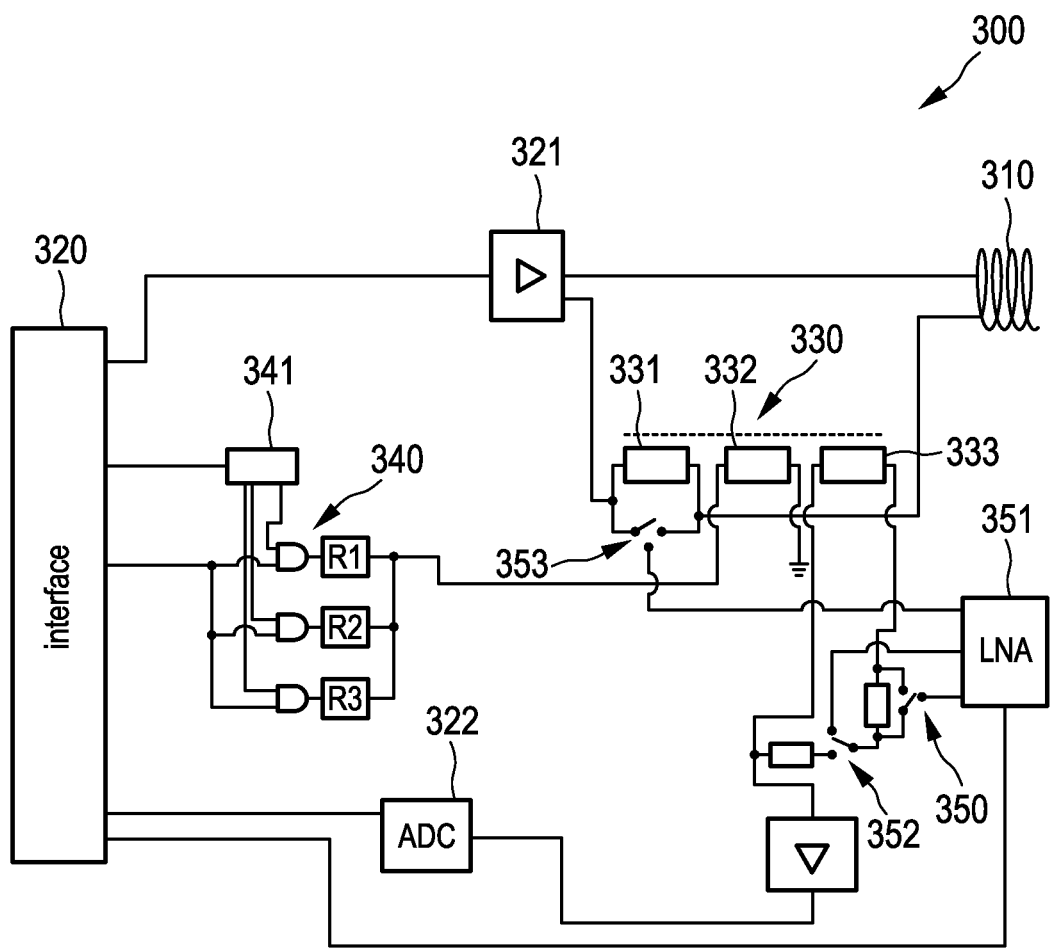
FIG. 3 shows schematically and exemplarily an embodiment of a sending/receiving circuitry of an additional coil.

FIG. 3 shows schematically and exemplarily an embodiment of sending/receiving circuitry 300 of an additional coil 310. Sending/receiving circuitry 300 refers to a combination of a receiving circuitry for receiving an electromagnetic signal and generating an electric signal indicative of the received electromagnetic signal, and a sending circuitry for generating from a provided electric signal a current that when provided to the additional coil 310 leads to the sending of an electromagnetic signal. The exemplary sending/receiving circuitry 300 shown in FIG. 3 comprises a computer interface 320 which can provide electric signals for controlling the sending/receiving circuitry and/or the additional coil 310 or for receiving and further processing the electric signals indicative of an electromagnetic signal received by the additional coil 310, for example from controller 134 of FIG. 1. Each connecting line between two components of the sending/receiving circuitry 300 can be regarded as one or more data line for transporting electric signals, i.e. electric currents, between the different components. A first electric signal is provided from the computer interface 320 to an amplifier 321 that can be realized as an H-bridge, i.e. full bridge. The output signal of the amplifier 321 is then provided to a transformer 330 and from the transformer 330 to the additional coil 310 for providing a base signal, which can be, for instance, the electromagnetic excitation signal. The transformer 330 can be regarded as an interface between the additional coil 310 and further parts of the sending/receiving circuitry that are used for modifying the received or provided electric signals such that the additional coil 310 can be used for receiving/sending the electromagnetic localization signal and also for receiving the electromagnetic response signal of the magneto-mechanical oscillator and/or for sending the electromagnetic excitation signal.

In particular, an electric signal coming from or going to the additional coil 310 passes a first inductance 331 of the transformer 330 and accordingly is coupled to the other inductances 332, 333 of the transformer 330. Accordingly, the transformer 330 in this example allows for an inductive coupling between the additional coil 310 and other parts of the sending/receiving circuitry 300. However, in other embodiments also other electric couplings can be utilized, for instance, capacitive couplings or resistive couplings.

A further part of the sending/receiving circuitry 300 can be regarded as a sending circuitry for sending the electromagnetic localization signal. In this part of the circuitry an electric signal that leads to the electromagnetic localization signal is provided by the computer interface 320 to circuitry element 340 comprising a logical AND gate 341 and three resistors R1, R2 and R3. The resistors R1, R2 and R3 control which current is provided to the second inductance 332 of the transformer 330, based on the electric signal received by the circuitry element 340, and thus how the base signal is modified to result in an electromagnetic localization signal sent by the additional coil 310. Generally, it is beneficial that the resistors R1, R2, R3 comprise a higher impedance when compared with the impedance of the second inductance 332 at the frequency of interest, such that a relatively weak coupling is achieved with the first inductance 331.

A third part of the sending/receiving circuitry 300 can be regarded as a receiving circuitry that allows for receiving the electromagnetic localization signal without exceeding a saturation threshold of the receiving circuitry. In this part, the third inductance 333 of the transformer 330 allows for receiving an electric signal indicative of an electromagnetic signal received by the additional coil 310 over an inductive coupling with the first inductance 331. The electric signal decoupled from the additional coil 310 by the third inductance 333 can directly be provided to a low noise amplifier (LNA) 351 being part of a circuitry element 350. Alternatively, the decoupled electric signal can also be provided first to a damping element 352 which is here realized as a potentiometer being part of the circuitry element 350 before being provided to the LNA 351 and then finally over an analog to digital converter 322 to the computer interface 320. Which of the possible two paths is used for the decoupled, i.e. received signal, can be determined by controlling the switches shown as part of the damping element 352. Thus, these two paths allow for two different damping factors of the received signal, i.e. to two different amplifications. Generally, adjustable damping elements also can be provided that allow for more than two damping factors and thus for an even higher accuracy and flexibility of the additional coil 310. Here, LNA may comprise a junction-gate field-effect transistor (JFET) (common source amplifier) input stage and some low noise operational amplifier for further amplification. However, in various embodiments other amplifiers may be employed (for example having a silicon bipolar input stage).

Generally, all switches shown in this exemplary sending/receiving circuitry 300 refer to commonly known computationally controllable switches. For instance, they can be realized as a mechanical or semiconductor relay. Optionally, the LNA 351 can be adapted to control a further switch 353 which can short circuit the inductance 331. This can be advantageous if the LNA 351 is to be protected during the sending of an electromagnetic signal. Further, a slow rising of the current in the additional coil 310 due to inductance 331 can be prevented for small currents during the spending. Generally, it is beneficial that the first inductance 331 comprises an inductivity that is much higher than the inductivity of the second and third inductances 332, 333, more beneficially at least 10 times higher. This allows also an acceptable protection of the LNA 351 without the optional switch 353.

Generally, tracking of magneto-mechanical oscillators relies on the spatially resolved detection of the response of a magneto-mechanical oscillator, for instance, to a series of excitation pulses. The spatial information is typically obtained by using an array of main receiving coils with known spatial sensitivity profiles. While for general-purpose applications a compromise between spatial resolution and technical effort of the main coil array and detection system may lead to a limited number of rather large main coils, for some applications a higher resolution may be needed for a short time, e.g. when inserting a needle into a patient. Finer coil arrays provide higher resolution and sensitivity especially if they are close to the workspace. However, it is inconvenient to place them in the workspace all the time as they may interfere with the workflow of the procedure.

To provide a more flexible system for receiving the signals of a magneto-mechanical oscillators, it is proposed, for instance, to provide a set of additional coils. The additional coils can be physically connected to one or more of the main coils or main coil arrays. Beneficially, each additional coil comprises signal reception means, i.e. a receiving circuitry, that is adapted to not being saturated during at least the weakest excitation signal sent by the main sending coil. By sensitivity encoding, the position and orientation of the additional coils can be deduced from the signal, i.e. the received localization signal, detected from an electromagnetic localization signal sent using the main coil array. The determined position and/or orientation of the additional coils can then be incorporated in a position and property reconstruction computational model of a reconstruction algorithm that is used for localizing the magneto-mechanical oscillator. Moreover, the main sending coil can be controlled to utilize a low power transmit mode in order to improve the position and orientation determination if necessary. In this case, the low power transmit mode comprises sending a pilot tone signal as an electromagnetic localization signal that has an amplitude that is low enough to not saturate a receiving circuitry of the additional coils. Generally, the additional coils can be provided as wireless coils or can be provided with a wire connection interface. In the latter case, it is beneficial that the additional coils are also provided with a sending functionality, i.e. a sending circuitry, for instance, for sending an excitation signal or an electromagnetic localization signal.

As the additional coils may be placed at a region of interest of a patient and thus move during a tracking of the location of magneto-mechanical oscillator, the position and/or orientation information is beneficially updated at sufficiently high frequency. Motion models indicative of an expected motion can be employed to reduce the need for frequently solving the full coil localization problem.

Beneficially, the reconstruction for determining the positions and/or orientations is performed by a general model-based reconstruction algorithm as known for localizing the source of an electromagnetic signal. This algorithm is based on sensitivity information for each additional coil, which beneficially is pre-recorded and/or obtained in a calibration operation, wherein a calibration operation may be performed in conjunction with each measurement pulse. In a simple embodiment, all main sending coils can send a "pilot tone" as an electromagnetic localization signal that refers to a constant signal outside a normal operation band of the main coils, i.e. outside the band of the normally used electromagnetic excitation signal. This pilot tone can be sequentially sent by all the main sending coils and at least be recorded by the additional coils, and can be sent prior to each measurement pulse (so the "calibration" as such is performed before each measurement). This offers maximum position accuracy, since the time delay between calibration and measurement is minimum (reduce errors due to motion). This can be done constantly even during a magneto-mechanical oscillator signal reception. With this information, the general reconstruction algorithm utilized, for instance, by the processor, can place and orient the additional coils and the result will be accurate due to the high signal-to-noise ratio. The pilot tone can be sent by the movable coil or coils in the fixed array. One example procedure may be as follows:

Send pilot tone/calibration magnetic signal (can be done by movable coil or coils in the fixed array)

Send measurement signal (any combination of coils including the movable coil)

Receive pilot tone/calibration signal (any combination of coils) and generate corresponding electrical calibration signals Receive sensor response (any combination of coils including the movable coils, and generate corresponding electrical sensors signals).

Process calibration signal to obtain calibration information (a.k.a. sensitivity profile by the sensitivity provider).

Use calibration signal in processing electrical sensors signals to determine sensor position In some embodiments, an upgrade kit may be provided for use with an existing system which includes for use with a system as described above which comprises a main coil array, wherein the main coil array comprises a main receiving coil which is configured to receive an electromagnetic response signal of a magneto-mechanical oscillator, and wherein the main coil array further comprises a main sending coil which is configured to transmit an electromagnetic excitation signal for exciting the magneto-mechanical oscillator. Such a kit may comprise at least one moveable additional coil which is configured to be placed in a region of interest with respect to the magneto-mechanical oscillator and is configured to transmit an additional electromagnetic excitation signal for exciting the magneto-mechanical oscillator and/or receive the electromagnetic response signal of a magneto-mechanical oscillator. The upgrade kit may further comprise at least one non-transitory, tangible, medium having stored thereon program code which is executable to cause at least one of the main sending coil and the at least one moveable additional coil to transmit an electromagnetic localization signal, and to provide from at least one of the at least one moveable additional coil and the main receiving coil a received localization signal, and is further executable for causing a processor to locate at least one of a position and an orientation of the at least one moveable additional coil from the received localization signal. Here, the electromagnetic localization signal may be a pilot tone signal, as described above. In some embodiments, the at least one non-transitory, tangible, medium may have further stored thereon information about one or more construction properties of the at least one moveable additional coil, wherein the one or more construction properties include at least one of a diameter and a number of windings of the at least one moveable additional coil. In some embodiments, the program code may be further configured to cause the processor to determine sensitivity information of the at least one additional coil for the electromagnetic response signal based at least in part on the one or more construction properties of the at least one moveable additional coil and further based on the at least one position and orientation of the at least one moveable additional coil. In some embodiments, the electromagnetic excitation signal is transmitted repeatedly and the program code is executable to cause the electromagnetic localization signal to be transmitted repeatedly, prior to the repeated transmissions of the electromagnetic excitation signal.

Further, additional algorithms mitigating effects due to metal in the surrounding environment can also be applied by the processor as part of the position and/or orientation determination. Moreover, the processor can be adapted to use the known position and/or orientation of a first additional coil in a computational model-based reconstruction algorithm to further reconstruct a position and/or orientation of a second additional coil. The advantage is that with this approach, the field of view of the system can be gradually extended.

Furthermore, it is beneficial to extend the field of view of the system by incorporating an accelerometer in each of the additional coils. Moreover, instead of using the pilot tone as described above, in other embodiments also the excitation signal can be used for localizing the additional coils. In this embodiment, it is beneficial that the main sending coils are adapted to provide a low sending amplitude. Alternatively or additionally, the additional coils are beneficially provided with a switchable attenuator as part of a receiving path of a receiving circuitry of the additional coils. To avoid a saturation of a receiving circuitry of the additional coils, pilot tones as electromagnetic localization signal can be used that comprise an adjustable power level. The system has the highest flexibility if the additional coils may be configured for being sending coils. This can be achieved in a simple way by providing the additional coils with a wired connection to a power supply. Alternatively, the additional coils can also be provided with batteries as power storage. A battery-operated additional coil is much more convenient for incorporating radiofrequency means to transmit the received signal. Moreover, the main sending coils can also be used to transmit power to the additional coils to charge a local energy storage of the additional coils, for example, a battery or double layer capacitor. Moreover, the additional coils can also be provided with an LC resonator. The resonator can be tuned approximately to the sending frequency of the magneto-mechanical oscillator and can locally enhance sending and receiving fields.

Devices which employ pilot tones as disclosed herein may provide many benefits and advantages, and the applications are not limited to the ones described in this application. For instance, the pilot tones can be used for compensation of a drift of the receiver coil, compensation of a drift of an amplifier and other purposes. In some cases, the drift could be a gain drift and the amplifier 321 and/or the low noise amplifier (LNA) 351 could be utilized. It is generally known that LNA drift is compensated within the LNA by a suitable feedback and that it can be used to boost the received signal to a sufficient level above the noise floor so that the amplifier can be used for additional processing. However, this inherently creates noise and/or power draining (power penalty) that is not desirable in these kinds of systems. By using the pilot tone construction, these negative effects can be minimized or avoided altogether. Furthermore, the construction and pilot tones allows detection of the presence of a disturbance near the coils, e.g. main or additional coils or the combination of the two (for example disturbances which can be caused by the presence of metals in the environment). This in-turn allows the risk to patients (for example in heart procedures) to be reduced or minimized, signal reliability to be increased, noise to be decreased, etc. Furthermore, the presence of metals in the area not only changes the gain in a coil but also the spectral response of the coils. By utilizing the structure of pilot tones, it is possible to separate the generally undesirable signals like noise signals from the desirable signals like the response signals. For instance, in the previous example, the signal produced from metal in the vicinity of the coils can be distinguished from a low noise amplifier (LNA) 351 gain change.

Furthermore, the inventors have determined that, surprisingly, it is possible to generate pulses of a sufficiently high strength that they can be used and detected by other coils, such as the array coils. This can be done in such a manner that receiving signals, such as self-receiving signals, are not saturated. In some advantageous embodiments this allows permanently localizing coils in relation to each other, wherein the coils could be main coils, additional coils or any combination of such. In some advantageous embodiments, it is further desired to filter pulses before performing coupling into the coils. Preferably, the pulses are low-pass filtered as is known in the art. This allows generation of pulses strong enough to be measured by the other coils while not saturating its own receive operation. In some embodiments the other coils are additional coils; in other embodiments those are main coils in the array.

In some embodiments, complementary metal-oxide-semiconductor (CMOS) devices can be used in generating pilot tones, wherein there might be different types of CMOS devices utilized, such as RF CMOS devices. In some embodiments, CMOS output logical gates can be utilized for pilot tone generation. For example, the CMOS gates may connect the output to the stable ground. This would allow that the supply (e.g., Vcc) voltage potential at the given resistor does not produce a voltage drop. Advantageously, this configuration may provide stability to the system. In some instances, it would only be necessary to stabilize Vcc to a stable level in order to stabilize the whole system. Generally, this may be done by utilizing simple-design and cost-effective voltage regulators. Hence, this may provide the additional advantage of being cost-effective. In some embodiments, voltage regulators can be additionally utilized, whereas the regulators can be regulators which exhibit low-temperature drift.

Figure 4:
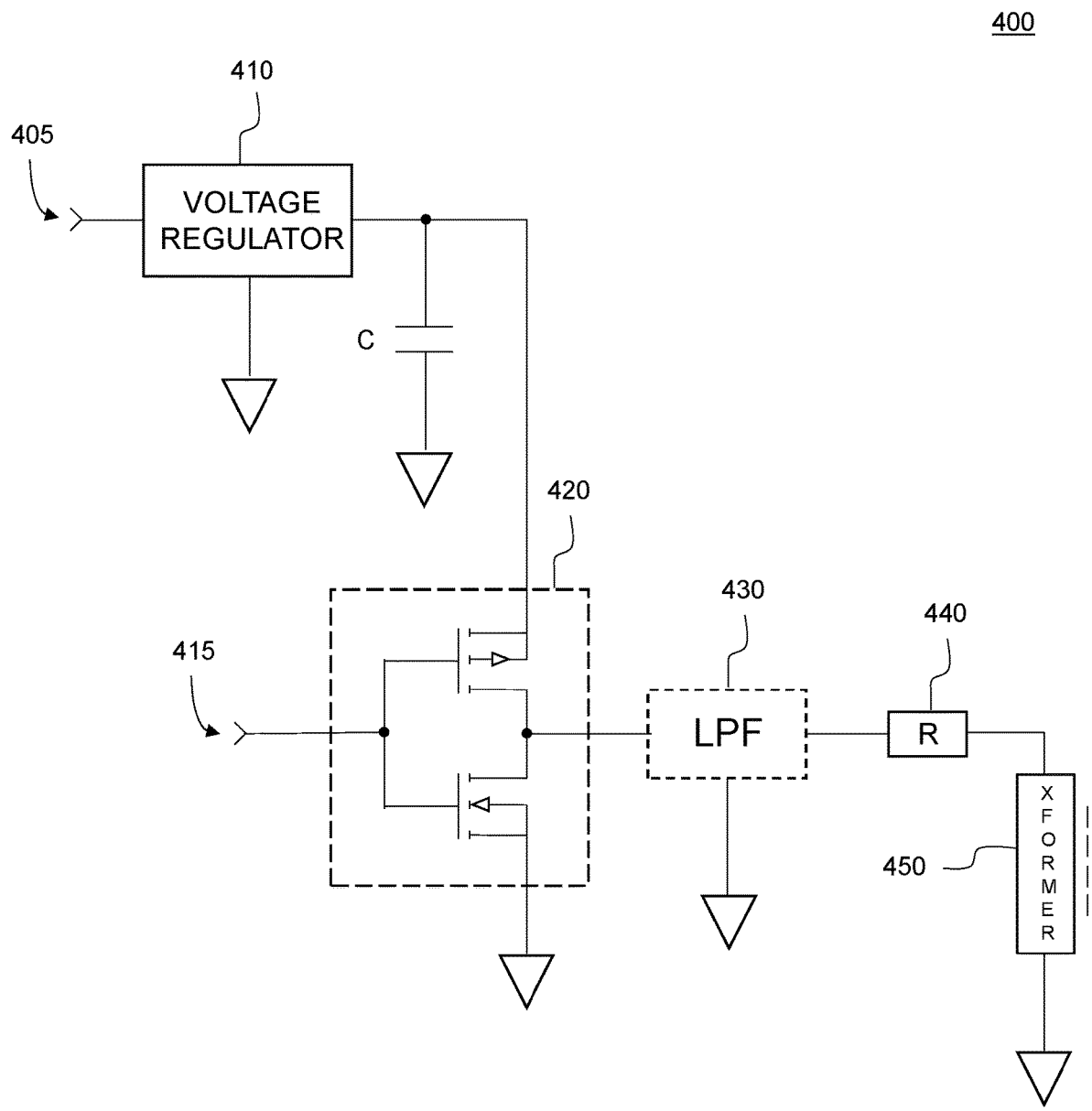
FIG. 4 show schematically and exemplarily an embodiment of a pilot tone generation circuit.

FIG. 4 show schematically and exemplarily an embodiment of a pilot tone generation circuit 400 which is configured to generate a pilot tone signal which may be employed as electromagnetic localization signal as described above. Pilot tone generation circuit 400 comprises a voltage regulator 410, a CMOS output stage device 420, an optional low pass filter (LPF) 430, a resistor R 440, and a coupling transformer 450. Voltage regulator has an input 405 which receives a power voltage and in response thereto produces a regulated supply voltage Vcc. Voltage regulator 410 may be a precision voltage regulator. A capacitor C at the output of voltage regulator 410 may reduce noise and stabilize the regulated supply voltage Vcc. CMOS output stage device 420 has an input 415 which receives a pilot-tone input signal. The pilot tone input signal may be a digital signal comprising, for example, a sequence of pulses which is unique to each coil which transmits a pilot tone signal. Beneficially, the transistors of CMOS output stage device 420 have an ON resistance which is much less (e.g., by one or more orders of magnitude) than the resistance of resistor R 440. Coupling transformer 450 couples the pilot tone output signal to the send/receive coil system.

As there are different purposes for the pilot tone, in some embodiments circuit 400 may be modified to implement different current levels that can be selected. In some embodiments, the actual pilot tone signal and a control signal are employed, that allows for different current levels to be selected. In that case, the circuit includes different outputs with different output resistors and they are combined in parallel. A digital control signal (for example, a two bit word) selects the appropriate output stage.

Although in the above embodiments, the system comprises an additional coil array comprising three additional coils, in other embodiments the system can comprise any number of additional coils, for instance, only one additional coil, or a plurality of additional coils. Moreover, although in the above embodiments the system comprises only one main sending coil, in other embodiments the system can comprise more than one main sending coil, in particular, a plurality of main sending coils, wherein in this case the same principles as described in detail above can be applied. Moreover, although in the above embodiments the system comprises a main receiving coil array comprising three main receiving coils, in other embodiments the system can comprise any number of main receiving coils, for instance, one main receiving coil, or a plurality of main receiving coils. In particular, although in the above embodiments the system comprises a main sending coil that is only used for sending electromagnetic signals and main receiving coils that are only used for receiving electromagnetic signals, in other embodiments each main coil of the system can be adapted to both be utilized as a main sending coil and as a main receiving coil.

Although in the above embodiment, the sending/receiving circuitry was described as part of the additional coil, in other embodiments the same or a similar sending/receiving circuitry can also be provided as part of the main coils or the main coil array. Moreover, although in the above embodiment a combination of a receiving circuitry and a sending circuitry was described as sending/receiving circuitry, in other embodiments the additional coil and/or the main coils can be provided with only a part of the sending/receiving circuitry, for instance, with only the receiving circuitry.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Procedures like the providing of sensitivity information, the providing of a motion model, the controlling of the coils, the determination of the positions and/or orientations of the additional coil, etc., performed by one or several units or devices can also be performed by any other number of units or devices. These processes can be implemented via program code of a computer program which may be stored in memory and is executed by a processor, and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

Disclosed herein is a system for receiving signals from a magneto-mechanical oscillator. The system comprises a main coil array adapted to receive a response signal of the magneto-mechanical oscillator and to send an excitation signal to the magneto-mechanical oscillator, and an additional coil for receiving a signal of the magneto-mechanical oscillator. A localizer is adapted to localize the additional coil and comprises a controller for controlling the main coil array and the additional coil such that a received localization signal is generated, a sensitivity provider for providing sensitivity information, and a processor for determining a position and/or orientation of the additional coil based on the provided sensitivity information and based on the received localization signal. The system can be applied flexibly and can be adapted easily to different medical situations.

The invention claimed is:

1. A system for receiving signals from a magneto-mechanical oscillator, wherein the system comprises:
 a main coil array, wherein the main coil array comprises at least one main sending coil which is configured to transmit an electromagnetic excitation signal for exciting the magneto-mechanical oscillator, and a main receiving coil, wherein the main receiving coil is configured to receive an electromagnetic response signal of the magneto-mechanical oscillator;
 at least one additional coil, wherein the additional coil is configured to at least one of: (1) receive the electromagnetic response signal of the magneto-mechanical oscillator; or (2) transmit the electromagnetic excitation signal for exciting the magneto-mechanical oscillator, wherein the main coil array and the additional coil form a medical coil system for receiving signals from the magneto-mechanical oscillator;
 a controller, wherein the controller is configured to control at least one of the main sending coil and the additional coil to transmit an electromagnetic localization signal, and is further configured to control the additional coil to generate a received localization signal which is indicative of the electromagnetic localization signal received by the additional coil in response to the controller controlling the main sending coil to transmit the electromagnetic localization signal, and to control the main receiving coil to generate a received localization signal which is indicative of the electromagnetic localization signal received by the main receiving coil in response to the controller controlling the additional coil to transmit the electromagnetic localization signal; and
 a processor, wherein the processor is configured to determine at least one of a position or an orientation of the additional coil based on the received localization signal and based on sensitivity information, wherein the sensitivity information is indicative of a sensitivity profile of at least one of: (1) the additional coil and the main sending coil, respectively, in case the controller controls the main sending coil to transmit the electromagnetic localization signal, or (2) the additional coil and the main receiving coil, respectively, in case the controller controls the additional coil to transmit the electromagnetic localization signal.

2. The system of claim 1, wherein the additional coil comprises a receiving circuit, wherein the receiving circuit is configured to receive an electromagnetic signal and to generate an electric signal indicative of the received electromagnetic signal, wherein the receiving circuitry has a saturation threshold, and wherein the receiving circuit is configured such that the saturation threshold is not reached in response to the receiving circuit receiving the electromagnetic excitation signal sent by the main transmitting coil, and the receiving circuit generates an electric signal indicative of the electromagnetic excitation signal.

3. The system of claim 1, wherein the controller is configured to control at least one of the main sending coil and the additional coil such that the electromagnetic localization signal is transmitted repeatedly with a predetermined time period between transmissions of the electromagnetic localization signal, and is further configured to control at least one of the additional coil and the main receiving coil, respectively, to generate the received localization signal based on the received electromagnetic localization signal from the transmissions of the electromagnetic localization signal, and wherein the processor is configured to determine the at least one of the position and the orientation of the additional coil based on the received localization signal generated from the transmissions of the electromagnetic localization signal.

4. The system of claim 1, wherein the electromagnetic localization signal comprises a sequence of signals, and utilizes varying pulse patterns.

5. The system of claim 1, wherein the localization signals are filtered.

6. The system of claim 1, wherein at least one of the at least one main sending coil and the at least one additional coil is configured to generate and transmit a pilot tone signal as the electromagnetic localization signal, wherein the pilot tone signal has frequencies which lie outside of a frequency range of the electromagnetic excitation signal.

7. The system of claim 6, wherein the at least one of the at least one main sending coil and the at least one additional coil includes a CMOS output logic circuit which is configured to generate the pilot tone signal.

8. The system of claim 1, wherein at least one of: (1) the at least one main sending coil comprises a main sending coil array having a plurality of main sending coils, and the controller is configured to control the main sending coil array such that the main sending coils of the main sending coil array sequentially transmit an electromagnetic localization signal, and is further configured to control the additional coil to generate for at least some of the sequentially received electromagnetic localization signals a received localization signal; or (2) the at least one additional coil comprises an additional coil array having a plurality of additional coils, and the controller is configured to control the additional coil array such that the additional coils of the additional coil array sequentially transmit an electromagnetic localization signal, and is further configured to control the main receiving coil to generate for at least some of the sequentially received electromagnetic localization signals a received localization signal, and
 wherein the processor is adapted to further determine at least one of a position and an orientation of the additional coil based on the generated received localization signals.

9. The system of claim 1, wherein the processor is configured to receive a motion model, wherein the motion model is indicative of a movement of a region of interest to which the additional coil is attached, and wherein the processor is configured to determine at least one of a current position and orientation of the additional coil further based on the motion model.

10. The system of claim 1, wherein the additional coil further comprises an accelerometer, wherein the accelerometer is configured to measure an acceleration of the additional coil, and wherein the processor is adapted to determine at least one of a current position and orientation of the additional coil further based on the measured acceleration of the additional coil.

11. The system of claim 1, wherein the electromagnetic localization signal has an amplitude that does not saturate a receiving circuitry of at least one of the additional coil and the receiving coil, respectively, wherein the receiving circuitry is configured to receive an electromagnetic signal and to generate the received localization signal.

12. The system of claim 1, wherein the electromagnetic localization signal has signal characteristics that lie outside of a signal characteristic range utilized for the excitation of the magneto-mechanical oscillator.

13. The system of claim 1, wherein the electromagnetic excitation signal comprises the electromagnetic localization signal.

14. The system of claim 1, wherein the additional coil comprises a local energy storage element, wherein the local energy storage element is configured to be charged by an electromagnetic charge signal, and wherein the controller is configured to control the main sending coil to transmit the electromagnetic charge signal to the additional coil.

15. The system of claim 1, comprising an LC circuit, wherein LC circuit comprises the additional coil, wherein a resonance frequency of the LC circuit lies in a frequency range of the electromagnetic excitation signal.

16. A system configured to be used together with: (1) a main coil array, wherein the main coil array comprises a main receiving coil which is configured to receive an electromagnetic signal of a magneto-mechanical oscillator, and wherein the main coil array further comprises a main sending coil which is configured to transmit an electromagnetic excitation signal for exciting the magneto-mechanical oscillator, and (2) an additional coil, wherein the additional coil is configured to receive an electromagnetic response signal of the magneto-mechanical oscillator, wherein the system is adapted to localize the additional coil, wherein the system comprises:
- a controller, wherein the controller is configured to control at least one of the main sending coil and the additional coil to transmit an electromagnetic localization signal, and is further configured to control the additional coil to generate a received localization signal which is indicative of the electromagnetic localization signal received by the additional coil in response to the controller controlling the main sending coil to transmit the electromagnetic localization signal, and to control the main receiving coil to generate a received localization signal which is indicative of the electromagnetic localization signal received by the main receiving coil in response to the controller controlling the additional coil to transmit the electromagnetic localization signal; and
- a processor, wherein the processor is configured to determine at least one of a position and an orientation of the additional coil based on the received localization signal and based on sensitivity information, wherein the sensitivity information is indicative of a sensitivity profile of at least one of: (1) the additional coil and the main sending coil, respectively, in case the controller controls the main sending coil to transmit the electromagnetic localization signal, or (2) the additional coil and the main receiving coil, respectively, in case the controller controls the additional coil transmits to transmit the electromagnetic localization signal.

17. A method of operation of a system with: (1) a main coil array, wherein the main coil array comprises a main receiving coil which is configured to receive an electromagnetic response signal of a magneto-mechanical oscillator, and wherein the main coil array further comprises a main sending coil which is configured to transmit an electromagnetic excitation signal for exciting the magneto-mechanical oscillator, and (2) an additional coil, wherein the additional coil is configured to receive an electromagnetic response signal of the magneto-mechanical oscillator, wherein the system is configured to localize the additional coil, wherein the method comprises:
- controlling at least one of the main sending coil and the additional coil to transmit an electromagnetic localization signal;
- controlling the additional coil to generate a received localization signal which is indicative of the electromagnetic localization signal received by the additional coil in response to controlling the main sending coil to transmit the electromagnetic localization signal;
- controlling the main receiving coil to generate a received localization signal which is indicative of the electromagnetic localization signal received by the main receiving coil in response to controlling the additional coil to transmit the electromagnetic localization signal;
- providing sensitivity information, wherein the sensitivity information is indicative of a sensitivity profile of at least one of: (1) the additional coil and the main sending coil, respectively, in case of controlling the main sending coil to transmit the electromagnetic localization signal, and (2) the additional coil and the main receiving coil, respectively, in case of controlling the additional coil to transmit the electromagnetic localization signal; and
- determining at least one of a position and an orientation of the additional coil based on the provided sensitivity information, and based on the received localization signal.

18. A non-transitory, computer-readable medium having stored instructions which, when executed by one or more processors, cause the one or more processors to:
- control at least one of a main sending coil and an additional coil of a system to transmit an electromagnetic localization signal for exciting a magneto-mechanical oscillator,
  - wherein the system comprises a main coil array, wherein the main coil array comprises a main receiving coil which is configured to receive an electromagnetic response signal of the magneto-mechanical oscillator, and wherein the main coil array further comprises the main sending coil,
  - wherein the additional coil is configured to receive an electromagnetic response signal of the magneto-mechanical oscillator, and
  - wherein the system is configured to localize the additional coil;
- control the additional coil to generate a received localization signal which is indicative of the electromagnetic localization signal received by the additional coil in response to controlling the main sending coil to transmit the electromagnetic localization signal;
- control the main receiving coil to generate a received localization signal which is indicative of the electromagnetic localization signal received by the main receiving coil in response to controlling the additional coil to transmit the electromagnetic localization signal;
- provide sensitivity information, wherein the sensitivity information is indicative of a sensitivity profile of at least one of: (1) the additional coil and the main sending coil, respectively, in case of controlling the main sending coil to transmit the electromagnetic localization signal, and (2) the additional coil and the main receiving coil, respectively, in case of controlling the additional coil to transmit the electromagnetic localization signal; and
- determine at least one of a position and an orientation of the additional coil based on the provided sensitivity information, and based on the received localization signal.

* * * * *